United States Patent [19]

Cazaubon et al.

[11] Patent Number: 4,481,192

[45] Date of Patent: Nov. 6, 1984

[54] ACID-PROTEASE INHIBITING PEPTIDE DERIVATIVES

[75] Inventors: Catherine Cazaubon, Montpellier; Joseph Diaz, Perols; Rémy Guegan, Castelnau-le-Lez; Bernard Castro, Mauguio; Geneviève Evin; Pierre Corvol, both of Paris; Jean-Pierre Gagnol, St-Martin-de-Londres, all of France

[73] Assignees: SANOFI; Institut Nationale de la Sante et de la Recherche Medicale, both of Paris, France

[21] Appl. No.: 522,534

[22] Filed: Aug. 12, 1983

[30] Foreign Application Priority Data

Aug. 17, 1982 [FR] France ............................. 82 14219

[51] Int. Cl.³ .................... A61K 37/00; C07C 103/52
[52] U.S. Cl. ............................. 424/177; 260/112.5 R
[58] Field of Search ................. 260/112.5 R; 424/177

[56] References Cited

U.S. PATENT DOCUMENTS

| | | | |
|---|---|---|---|
| 3,840,516 | 10/1974 | Umezawa et al. | 260/112.5 R |
| 3,878,185 | 4/1975 | Murao et al. | 260/112.5 R |
| 3,907,764 | 9/1975 | Kakinuma et al. | 260/112.5 R |
| 4,348,386 | 9/1982 | Kojima et al. | 260/112.5 R |

*Primary Examiner*—Delbert R. Phillips
*Attorney, Agent, or Firm*—Bacon & Thomas

[57] ABSTRACT

The present invention relates to peptide derivatives of the general formula:

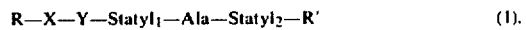

$$R-X-Y-Statyl_1-Ala-Statyl_2-R' \qquad (1).$$

in which:
  Statyl$_1$ and Statyl$_2$ represent the radical derived from the aminoacid statine,
  R denotes a hydrogen atom or an acylating group attached to the terminal amino group of the aminoacid X—,
  X and Y, which are identical or different, denote aminoacids of the L or D configuration if a center of asymmetry exists in the molecule, and optionally protected in their side chain, with the proviso that X and Y cannot simultaneously denote valine, and
  R' denotes OH, O-lower alkyl, NH$_2$ or a group NH-R$_1$, in which R$_1$ represents a lower alkyl or lower aralkyl group.

It also relates to a process for the preparation of the products of the formula (1) and to the medicaments containing a product of the formula (1) as the active principle.

6 Claims, No Drawings

ACID-PROTEASE INHIBITING PEPTIDE DERIVATIVES

In 1970, UMEZAWA isolated, from a streptomyces culture, a pentapeptide designated by the name pepstatine, the structure of which was subsequently established and corresponds to the formula:

Isovaleryl-L-Valyl-L-Valyl-Statyl-L-Alanyl-Statine, in which the name statine designates an unusual aminoacid, namely (3S,4S)-4-amino-3-hydroxy-6-methylheptanoic acid.

It has been shown that pepstatine is an inhibitor of acid proteases and acts, in particular, on pepsin and renin. In particular, renin, which is an enzyme of renal origin, is involved in the sequence angiotensinogen, angiotensin I, angiotensin II in the conversion of angiotensinogen to angiotensin.

As angiotensin is responsible for increasing the arterial pressure, it has been envisaged to use pepstatine for combating hypertension in man.

However, since pepstatine acts on all acid proteases, its use in therapy has proved difficult.

A few pepstatine derivatives have been described in the scientific literature. It seems, however, that their level of activity is generally relatively modest and their selectivity low.

The present invention relates to the preparation of new pepstatine derivatives having a high level of activity in the inhibition of renin and pepsin.

The compounds according to the invention correspond to the general formula:

R—X—Y—Statyl$_1$—Ala—Statyl$_2$—R'   (I)

in which Statyl$_1$ denotes the radical derived from the aminoacid statine, namely:

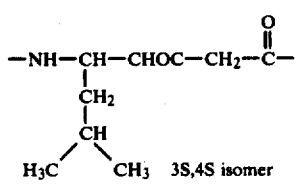

and Statyl$_2$ denotes the statyl radical derived from the same aminoacid, but can be the 3S,4S isomer or the 3R,4S isomer.

R denotes a hydrogen atom or an acylating group attached to the terminal amino group of the aminoacid X—.

More particularly, R can represent the following groups: acetyl (Ac), isovaleryl (iva), octyl, t-butylacetyl, t-butoxycarbonyl (Boc) adamantyloxycarbonyl (Adoc), benzyloxycarbonyl (Z), (benzyloxycarbonyl)-β-aminoethylsulphonyl (Z-Tau), (t-butoxycarbonyl)-β-amino-β ethylsulphonyl (Boc-Tau), phenylsulphonyl, benzylsulphonyl or 3-phenylpropionyl.

X and Y, which are identical or different, denote aminoacids of the L or D configuration when a centre of asymmetry exists in the molecule, and optionally protected in their side chain.

The preferred aminoacids are as follows:

X: Phenylalanine, Tryptophan, Histidine, Boc-Histidine, Tyrosine, Proline and Isoleucine, and Y: Phenylalanine, Tryptophan, Histidine, Tyrosine, Proline, Leucine, Isoleucine, Norleucine, Valine, Norvaline, Alanine, Glycine, Lysine, Z-Lysine and α-Aminobutyric acid, with the proviso that X and Y cannot simultaneously denote valine.

R' represents OH, O-lower alkyl, NH$_2$ or a group NH-R$_1$, in which R$_1$ represents a lower alkyl or lower aralkyl group.

The invention also includes the pharmaceutically acceptable salts which the compounds of the formula (I) may be able to give when R' represents OH.

The products according to the invention can be prepared in accordance with the usual methods of peptide chemistry. In particular, they can be prepared by a stepwise process from the terminal C.

The starting material is a lower alkyl ester of statine, with which the next aminoacid is condensed.

After the amine group of the dipeptide has been freed, the peptide chain is lengthened by coupling with the next aminoacid, suitably protected. Each coupling stage is followed by a selective operation for freeing the amine which will react to create the next peptide linkage.

The various coupling operations are carried out either using an activated ester of the aminoacid to be coupled, or using the N-protected aminoacid itself, in the presence of dicyclohexylcarbodiimide.

The stages of selective freeing of the amine are carried out either by hydrogenolysis or by hydrolysis in a strong acid medium such as trifluoroacetic acid, depending on the nature of the protecting group used.

Finally, if the aminoacid which is to be introduced into the sequence possesses, in its side chain, a functional group capable of reacting (this is the case of histidine in particular), the functional group should be blocked by a suitable protecting group, which is subsequently removed.

Finally, the peptides (I) in the acid form (R'=H) can be obtained from the corresponding esters by saponification in a dilute alkaline medium.

The non-limiting examples which follow are given by way of an illustration of the present invention.

In all these examples, the following abbreviations will be used:

AMINOACIDS AND PROTECTING OR ACTIVATING GROUPS

These abbreviations are in accordance with those indicated by the Nomenclature Commission of IUPAC-IUB, Biochemistry Section.

| Aminoacids: | |
|---|---|
| Ala | Alanine |
| His | Histidine |
| Ile | Isoleucine |
| Leu | Leucine |
| Nle | Norleucine |
| Nva | Norvaline |
| Phe | Phenylalanine |
| Pro | Proline |
| Sta | Statine |
| isoSta | Isostatine (3R,4S isomer) |
| Tau | Taurine |
| Trp | Tryptophan |
| Tyr | Tyrosine |
| Val | Valine |

Unless indicated otherwise, these aminoacids are of the L configuration. Those of the D series are indicated by (D) preceding the abbreviation.

| Protecting and activating groups: | |
|---|---|
| Ac | Acetyl |
| Adoc | Adamantyloxycarbonyl |
| Boc | t-Butoxycarbonyl |
| HONSu | N—Hydroxysuccinimide |
| OEt | Ethyl ester |
| OMe | Methyl ester |
| ONp | p-Nitrophenyl ester |
| ONSu | N—Hydroxysuccinimide ester |
| OTcp | 2,4,5-Trichlorophenyl ester |
| ivA | Isovaleryl |
| Z | Benzoyloxycarbonyl |

The following abbreviations will also be used:

| AcOEt | Ethyl acetate |
|---|---|
| AcOH | Acetic acid |
| AT | Ambient temperature |
| Bop | Benzotriazolyloxy-tris-dimethylamino-phosphonium hexafluorophosphate |
| DCCI | Dicyclohexylcarbodiimide |
| DCHA | Dicyclohexylamine |
| DCU | Dicyclohexylurea |
| DIPEA | Diisopropylethylamine |
| DMF | Dimethylformamide |
| DMSO | Dimethyl sulphoxide |
| Ether | Ethyl ether |
| HOBt | 1-Hydroxybenzotriazole |
| $KHSO_4$—$K_2SO_4$ | Aqueous solution containing 16.6 g of potassium bisulphate and 33.3 g of potassium sulphate per liter |
| MeOH | Methanol |
| NEM | N—Ethylmorpholine |
| TFA | Trifluoroacetic acid |
| TLC | Thin layer chromatography |

Finally, the nuclear magnetic resonance spectra were recorded at 250 MHz in solution in dimethyl sulphoxide, the internal standard being hexamethyldisiloxane.

The following abbreviations are used:

| s | singlet |
|---|---|
| d | doublet |
| m | multiplet or unresolved peaks |

EXAMPLE 1

Z—Phe—Phe—Sta—Ala—Sta—OMe (SR 41320)

1. Z—Ala—Sta—OMe 1.44 g of H—Sta—OMe.TFA, 595 mg of NEM, 2.06 g of Z—Ala—OTcp and 1.29 g of HOBt are dissolved in 35 ml of DMF at ambient temperature. The pH is adjusted to 6–7 to pH paper, if necessary, with NEM and the mixture is stirred at ambient temperature for 48 hours. The DMF is evaporated off in a water-bath at 40° under 0.01 mm. The residual oil is taken up in 50 ml of AcOEt and the latter is washed successively with 5% strength $KHSO_4$-$K_2SO_4$ solution, $NaCl/H_2O$, 5% strength $NaHCO_3$ solution and $NaCl/H_2O$. It is dried over $MgSO_4$ and the solvent is evaporated off.

The residue is taken up in ether and a solid appears. The mixture is left in a refrigerator for one hour and the solid is filtered off and dried.

Yield: 1.46 g (86%); M.p.: 117°–120° C.

2. H—Ala—Sta—OMe 1.46 g of Z—Ala—Sta—OMe are dissolved in 20 ml of MeOH, 1.03 g of ammonium formate are then added at ambient temperature, the mixture is stirred until a solution is obtained, 400 mg of 10% strength Pd/C are then added and the mixture is stirred for 5 minutes at ambient temperature. After 5 minutes, a TLC check shows the disappearance of the starting material. The pH is 8 to pH paper. The whole is filtered on a column of Amberlite IR 45 resin ($OH^-$) and the methanol is evaporated off.

The residue is taken up in ether and the mixture is evaporated to dryness. The rsidue is dissolved in methylene chloride, the insoluble material is filtered off and the filtrate is evaporated to dryness to give a white powder.

Yield: 810 mg (75%); M.p.: 123°–134° C.

3. Boc—Sta—Ala—Sta—OMe 960 mg of H—Ala—Sta—OMe, 1 g of Boc—Sta—OH, 420 mg of HONSu and 750 mg of DCCI are dissolved successively in 50 ml of methylene chloride at ambient temperature. A white precipitate appears very rapidly. The mixture is stirred at ambient temperature. After 7 hours, the DCU formed is filtered off and washed with methylene chloride. The organic solution is washed successively with $KHSO_4$-$K_2SO_4$ (5% strength solution in $H_2O$) and $NaHCO_3$ (5% strength solution in $H_2O$). It is dried over $MgSO_4$ and filtered and the solvent is evaporated off. The product is solubilised in the minimum amount of a 97.5/2.5 mixture of chloroform and MeOH and introduced into the top of a column (L: 24 cm; $\phi$: 2.5) charged with Merck $H^R$ type 60 silica gel using the same mixture. Elution is carried out with the same mixture and the eluate is fractionated.

This gives a batch of pure product (yield: 1 g) and two batches of product to be recycled under the same conditions.

Overall yield: 67%; M.p.: 95°–8° C.

4. H—Sta—Ala—Sta—OMe.TFA 1 g of Boc—Ala—Sta—OMe is solubilised in 5 ml of methylene chloride. 10 ml of TFA are added at ambient temperature and the mixture is then left for 30 minutes. The solvents are evaporated off under a waterpump vacuum. The residual oil is taken up in ether. The solid obtained is filtered off, rinsed with ether and dried.

Yield: 850 mg (85% ); M.p.: 148°–151° C.

5. Boc—Phe—Sta—Ala—Sta—OMe 470 g of H—Sta—Ala—Sta—OMe.TFA are covered with 50 ml of methylene chloride. 102 mg of NEM and 382 mg of Boc—Phe—ONSu are added. After one hour, since the product is difficult to solubilise, 10 ml of DMF are added; a check is carried out to ensure that the pH is 6–7 to pH paper; if not, it is adjusted with N-ethylmorpholine; the mixture is stirred for 20 hours at ambient temperature and the solvents are then evaporated off to dryness. The residue is dissolved in methylene chloride and this organic phase is washed successively with $KHSO_4$-$K_2SO_4$ solution, water, $NaHCO_3$ solution and water. It is dried over $Na_2SO_4$ and filtered and the solvent is evaporated off.

The residue is taken up in ether and the solid is filtered off and dried.

Yield: 410 mg (70%).

6. H—Phe—Sta—Ala—Sta—OMe.TFA 400 g of Boc—Phe—Sta—Ala—Sta—OMe are covered with 5 ml of TFA. When left for 20 minutes at ambient temperature, the solid rapidly solubilises. The solvent is evaporated off in vacuo. The residual oil is taken up in ether and the mixture is stirred. The solid obtained is filtered off, washed with ether and dried.

Yield: 400 mg (98%).

7. Z—Phe—Phe—Sta—Ala—Sta—OMe (SR 41320)

150 mg of H—Phe—Sta—Ala—Sta—OMe.TFA are solubilised in 10 ml of DMF. 25 mg of NEM are added, followed by 105 mg of Z—Phe—ONSu. The pH is adjusted to 6-7 to pH paper, if necessary, with NEM and the mixture is then stirred for 5 hours at ambient temperature. The solvent is evaporated off under a high vacuum, the residue is taken up in water and the solid obtained is filtered off, washed with water, dried and then washed with ether. It is dissolved in a 1/99 mixture of methanol and chloroform and introduced onto a column (L: 35 cm; $\phi$: 1 cm) containing Merck ®60 silica gel (70-230 mesh) in the same mixture. Elution is carried out with 150 ml of the same mixture and then with 100 ml of a 2/98 mixture of methanol and chloroform and 100 ml of a 3/97 mixture of methanol and chloroform. TLC is carried out and the pure fractions are evaporated. The residue is taken up in ether and the mixture is evaporated.

A white powder is obtained.

Yield: 130 mg (69%); M.p.: 188°-191° C.

EXAMPLE 2

Z—Phe—Phe—Sta—Ala—Sta—OH (SR 41225)

110 mg of Z—Phe—Phe—Sta—Ala—Sta—OMe (Example 1) are solubilised in 5 ml of DMF. 2 ml of water are added. 0.2 ml of normal sodium hydroxide solution is then added at ambient temperature; the mixture is stirred for 30 minutes at ambient temperature and 0.2 ml of N HCl is then added; the pH falls from 12.5 to 6.5. The solvents are evaporated off, the residue is taken up in water and the solid is filtered off, washed with water and dried.

| Yield: 70 mg (64%); | | |
|---|---|---|
| Aminoacid analysis: | Ala | 1.03 (1) |
| | Phe | 2.05 (2) |
| | Sta | 1.92 (2) |

EXAMPLE 3

Z—Phe—(D)Phe—Sta—Ala—Sta—OMe (SR 41330)

1. Boc—(D)Phe—Sta—Ala—Sta—OMe 470 mg of H—Sta—Ala—Sta—OMe.TFA (Example 1-4) are covered with 50 ml of dioxane. 102 mg of NEM are added, followed by 382 mg of Boc—(D)-Phe—ONSu. The mixture is stirred at ambient temperature. After 24 hours, the solvent is evaporated off, the residue is taken up in methylene chloride and the latter is washed successively with $KHSO_4$-$K_2SO_4$ solution, water, $NaHCO_3$ solution and water. It is dried over $Na_2SO_4$ and the solvent is evaporated off. The residue is taken up in ether and the mixture is evaporated. The residue is again taken up in ether, pentane is added and the solid obtained is filtered off, dissolved in chloroform and introduced into the top of a column containing Merck ®60 silica gel (70-230 mesh) in chloroform (L: 10 cm; $\phi$: 3 cm). Elution is carried out with chloroform and then with a 1/99 mixture of methanol and chloroform; the eluate is fractionated. The pure fractions are evaporated. The residue is taken up in ether/pentane and the solid is filtered off and dried.

Yield: 200 mg (37%).

2. H—(D)Phe—Sta—Ala—sta—OMe.TFA 200 mg of Boc—(D)Phe—Sta—Ala—Sta—OMe are covered with 2 ml of TFA. After 30 minutes at ambient temperature, the solvent is evaporated off, the residue is taken up in ether and the white solid obtained is filtered off and dried.

Yield: 190 mg (93%).

3. Z—Phe—(D)Phe—Sta—Ala—Sta—OMe (SR 41330)

190 mg of H—(D)Phe—Sta—Ala—Sta—OMe.TFA are solubilised in 25 ml of dioxane containing 64 mg of NEM. 133 mg of Z—Phe—ONSu and 45 mg of HOBt are added and the mixture is stirred at ambient temperature. The pH is adjusted to 6-7, if necessary, with NEM. After 24 hours, the solvent is evaporated off, the residue is taken up in water and triturated, the mixture is left to stand for 30 minutes and the solid is filtered off, washed with ether and dried.

| Yield: | 190 mg. |
|---|---|
| Aminoacid analysis: | Ala: 0.97 (1) |
| | Phe: 2.00 (2) |
| | Sta: 2.14 (2) |

NMR spectrum:

| $\delta$ | appearance | integration | assignment |
|---|---|---|---|
| 0.75 | m | 12 H | $^6C(CH_3)_2$ Sta |
| 1.09-1.60 | m | 9 H | $^5CH_2$ $^6CH$ Sta<br>$CH_3$ Ala |
| 2.08-2.37 | m | 4 H | $^2CH_2$ Sta |
| 2.43-3.05 | m | 4 H | $^3CH_2$ Phe |
| 3.49 | s | 3 H | $CH_3$ ester |
| 3.79 | m | 4 H | $^4CH$—$^3CH$ Sta |
| 4.16 | m | 2 H | $^2CH$ (D)Phe, Phe, Ala |
| 4.53 | m | 1 H | |
| 4.82 | d | | OH Sta |
| 4.85 | d | 4 H | $CH_2$ Z |
| 4.89 | d | | OH Sta |
| 7.04-7.26 | m | | aromatic protons |
| 7.31 | d | 17 H | NH |
| 7.36 | d | | NH |
| 7.52 | d | 1 H | NH |
| 7.84 | d | 1 H | NH |
| 8.27 | d | 1 H | NH |

EXAMPLE 4

Boc—Phe—Phe—Sta—Ala—Sta—OMe (SR 41331)

230 mg of H—Phe—Sta—Ala—Sta—OMe.TFA (Example 1-6) are solubilised in 25 ml of dioxane containing 80 mg of NEM. 145 mg of Boc—Phe—ONSu and 54 mg of HOBt are added, the mixture is stirred at ambient temperature and the pH is adjusted to 6-7, if necessary, with NEM. After 24 hours, the solvent is evaporated off and the residue is taken up in water and triturated. The mixture is left to stand for 30 minutes and the solid is filtered off, washed with water and then with ether and dried.

| Yield: | 180 mg (65%). |
|---|---|
| Aminoacid analysis: | Ala: 1.04 (1) |
| | Phe: 2.00 (2) |
| | Sta: 1.83 (2) |

NMR spectrum:

| $\delta$ | appearance | integration | assignment |
|---|---|---|---|
| 0.77 | m | 12 H | $^6C(CH_3)_2$ Sta |
| 1.02-1.58 | m | 18 H | $^5CH_2$—$^6CH$ Sta<br>$CH_3$ Ala<br>Boc Phe |
| 1.90-2.38 | m | 4 H | $^2CH_2$ Sta |
| 2.46-3.23 | m | 4 H | $^3CH_2$ Phe |
| 3.49 | s | 3 H | $CH_3$ ester |
| 3.74 | m | 4 H | $^4CH$—$^3CH$ Sta |

-continued

| | | | |
|---|---|---|---|
| 4.05 | m | 1 H | } $^2$CH Phe, Phe, Ala |
| 4.20 | m | 1 H | |
| 4.52 | m | 1 H | |
| 4.78 | d(J = 6 Hz) | 1 H | OH Sta |
| 4.93 | d(J = 6 Hz) | 1 H | OH Sta |
| 6.82 | d | 1 H | NH |
| 7.04 | m | 10 H | aromatic protons |
| 7.34 | d | 1 H | NH |
| 7.52 | d | 1 H | NH |
| 7.77 | d | 1 H | NH |
| 7.93 | d | 1 H | NH |

EXAMPLE 5

Boc—Trp—Trp—Sta—Ala—Sta—OMe (SR 41376)

1. Boc—Trp—Sta—Ala—Sta—OMe 470 mg of H—Sta—Ala—Sta—OMe.TFA (Example 1-4) are solubilised in 50 ml of dioxane containing 102 mg of NEM. 380 mg of Boc—Trp—ONp and 120 mg of HOBt are added. The mixture is stirred at ambient temperature and the pH is adjusted to 6-7, if necessary, with NEM. After 48 hours, the solvent is evaporated off in vacuo and the residue is taken up in chloroform and introduced into the top of a column containing Merck ®60 silica gel (70-230 mesh) in chloroform (L: 15 cm; φ: 3 cm). Elution is carried out with 300 ml of chloroform, 200 ml of a 1/99 mixture of methanol and chloroform, 200 ml of a 2/98 mixture of methanol and chloroform, 200 ml of a 3/97 mixture of methanol and chloroform and 500 ml of a 5/95 mixture of methanol and chloroform. The eluate is divided up into 25 ml fractions, which are monitored by TLC, the pure fractions are evaporated, the residue is taken up in pentane containing a small amount of ether, and the solid is filtered off and dried.

Yield: 320 mg (56%).

2. H—Trp—Sta—Ala—Sta—OMe.TFA 200 mg of Boc—Trp—Sta—Ala—Sta—OMe.TFA are covered with 5 ml of methylene chloride, to which 4 drops of ethanedithiol and 2 drops of anisol are added, followed by 2 ml of TFA. The mixture is left at ambient temperature, the solvents are evaporated off and the residue is taken up in ether. The solid is filtered off, washed copiously with ether and dried.

Yield: 170 mg.

3. Boc—Trp—Trp—Sta—Ala—Sta—OMe (Sr 41376)

170 mg of H—Trp—Sta—Ala—Sta—OMe.TFA are covered with 30 ml of dioxane containing 60 mg of NEM. 117 mg of Boc—Trp—ONp and 38 mg of HOBt are added. The mixture is stirred at ambient temperature and the pH is adjusted to 6-7, if necessary, with NEM. After 24 hours, the solvent is evaporated off and the residue is taken up in water; the mixture is left to stand. The solid obtained is filtered off and dissolved in methylene chloride and the organic solution is washed with KHSO$_4$-K$_2$SO$_4$ solution, water, NaHCO$_3$ solution and water. It is dried over Na$_2$SO$_4$ and the solvent is evaporated off. The product is dissolved in 3 ml of chloroform and introduced into the top of a column (L: 30 cm; φ: 2 cm) containing Merck ®60 silica gel (70-230 mesh) in chloroform. Elution is carried out with 100 ml of chloroform, 100 ml of a 1/99 mixture of methanol and chloroform and a 5/95 mixture of methanol and chloroform until the product is eluted. The eluate is fractionated and the pure fractions are evaporated. The residue is taken up in ether and the solid is filtered off and dried.

| | |
|---|---|
| Yield: | 90 mg (44%). |
| Aminoacid analysis: | Ala: 0.98 (1) |
| | Trp: 2.08 (2) |
| | Sta: 1.97 (2) |

NMR spectrum:

| δ | appearance | integration | assignment |
|---|---|---|---|
| 0.69-0.85 | m | 12 H | $^6$C(CH$_3$)$_2$ Sta |
| 0.93-1.58 | m | 18 H | { CH$_3$ Ala<br>$^5$CH$_2$—$^6$CH Sta<br>(CH$_3$)$_3$C Boc |
| 1.90-2.38 | m | 4 H | $^2$CH$_2$ Sta |
| 2.69-3.15 | m | 4 H | $^3$CH$_2$ Trp |
| 3.50 | s | 3 H | CH$_3$ ester |
| 3.71-3.89 | m | 4 H | $^4$CH—$^3$CH Sta |
| 4.00-4.27 | m | 2 H | $^2$CH Ala |
| 4.53 | m | 1 H | 2 × $^2$CH Trp |
| 4.75 | d | 2 H | 2 × OH Sta |
| 4.94 | d | | |
| 6.72-7.92 | m | 15 H | { aromatic protons<br>5 × NH |

EXAMPLE 6

Boc—(D)Phe—Val—Sta—Ala—Sta—OCH$_3$ (SR 41377)

1. Boc—Val—Sta—Ala—Sta—OMe 450 mg of H—Sta—Ala—Sta—OMe.TFA (Example 1-4) are covered with 50 ml of dioxane containing 211 mg of NEM. 314 mg of Boc—Val—ONSu and 135 mg of HOBt are added. The mixture is stirred at AT and the pH is adjusted to 6-7, if necessary, with NEM. After 24 hours, the solvent is evaporated off, the residue is taken up in water and the solid obtained is filtered off after 3 hours and dried. The crude product is dissolved in chloroform and introduced into the top of a column (L: 18 cm; φ: 3 cm) containing Merck ®60 silica gel (70-230 mesh) in the same solvent. Elution is carried out with mixtures of methanol and chloroform with a gradient up to 7/93 (volume/volume) in 200 ml fractions of solvent, and the eluate is fractionated. The pure fractions are evaporated.

Yield: 200 mg (38%).

2. H—Val—Sta—Ala—Sta—OMe 180 mg of Boc—Val—Sta—Ala—Sta—OMe are covered with 3 ml of TFA. After 30 minutes at ambient temperature, the solvent is evaporated off in the cold, the residue is taken up in ether and the white solid obtained is filtered off, washed with ether and dried.

Yield: 180 mg (100%).

3. Boc—(D)Phe—Val—Sta—Ala—Sta—OMe 150 mg of H—Val—Sta—Ala—Sta—OMe.TFA are covered with 35 ml of dioxane containing 90 mg of NEM. 101 mg of Boc—(D)Phe—ONSu and 38 mg of HOBt are added. 3 ml of DMF are added and the pH is adjusted to 6-7 with NEM. After 20 hours, the solvents are evaporated off, the residue is taken up in water and the solid obtained is filtered off, washed with water and then with ether and dried.

| | |
|---|---|
| Yield: | 150 mg (85%). |
| Aminoacid analysis: | Ala: 1.00 (1) |
| | Val: 1.08 (1) |
| | Phe: 0.97 (1) |
| | Sta: 1.96 (2) |

NMR spectrum:

-continued

| δ | appearance | integration | assignment |
|---|---|---|---|
| 0.67–0.83 | m | 18 H | $^6C(CH_3)_2$ Sta / $^3C(CH_3)_2$ Val |
| 1.09–1.58 | m | 18 H | $^5CH_2$—$^6CH$ Sta / $(CH_3)_3C$ Boc / $CH_3$ Ala |
| 1.92 | m | 1 H | $^3CH$ Val |
| 2.00–2.35 | m | 4 H | $^2CH_2$ Sta |
| 2.50–2.94 | m | 2 H | $^3CH_2$ (D)Phe |
| 3.50 | s | 3 H | $CH_3$ ester |
| 3.78 | m | 4 H | $^4CH$—$^3CH$ Sta |
| 4.08–4.26 | m | 3 H | $^2CH$ (D)Phe, Val, Ala |
| 4.75 | d | 1 H | OH Sta |
| 4.91 | d | 1 H | OH Sta |
| 6.90 | d | 1 H | NH |
| 7.06–7.33 | m | 6 H | aromatic protons + 1 NH |
| 7.50 | d | 1 H | NH |
| 7.75 | d | 1 H | NH |
| 7.82 | d | 1 H | NH |

EXAMPLE 7

Boc—Trp—(D)Trp—Sta—Ala—Sta—OMe (SR 41394)

1. Boc—(D)Trp—Sta—Ala—Sta—OMe 470 mg of H—Sta—Ala—Sta—OMe.TFA (Example 1-4) are covered with 50 ml of dioxane containing 195 mg of NEM; 380 mg of BOC—(D)Trp—ONp and 120 mg of HOBt are then added. The mixture is stirred at AT and the pH is adjusted to 6-7 to pH paper, if necessary, with NEM. After 6 days, the solvent is evaporated off, the residue is taken up in methylene chloride and the organic solution is washed successively with KHSO$_4$-K$_2$SO$_4$ solution, water, NaHCO$_3$ solution and water. It is dried over Na$_2$SO$_4$. The solvent is evaporated off to dryness and the product is dissolved in chloroform and introduced into the top of a column (L: 27 cm, φ: 2 cm) containing Merck ® silica gel (70–230 mesh) in chloroform. Elution is carried out with mixtures of methanol and chloroform with a gradient up to 5/95. The eluate is fractionated and the pure fractions are evaporated.

Yield: 330 mg (58%).

2. H—(D)Trp—Sta—Ala—Sta—OMe.TFA 220 mg of Boc—(D)Trp—Sta—Ala—Sta—OMe are covered with 10 ml of methylene chloride. 8 drops of ethanedithiol and 2 ml of TFA are added. After 30 minutes at AT, the solvents are evaporated off. The residue is taken up in ether, a small amount of pentane is added and the solid is filtered off, washed with ether and dried.

Yield: 210 mg (95%).

3. Boc—Trp—(D)Trp—Sta—Ala—Sta—OMe (SR 41394)

120 mg of H—(D)Trp—Sta—Ala—Sta—OMe.TFA are solubilised in 10 ml of dioxane containing 41 mg of NEM. 85 mg of Boc—Trp—ONp and 27 mg of HOBt are added. The mixture is stirred at AT and a check is made to ensure that the pH is 6-7 to pH paper; if not, it is adjusted with NEM. After 48 hours, the solvent is evaporated off, the residue is taken up in methylene chloride and the organic solution is washed successively with KHSO$_4$-K$_2$SO$_4$ solution, water, NaHCO$_3$ solution and water. It is dried over Na$_2$SO$_4$ and the solvent is evaporated off. The residue is dissolved in ethyl acetate and introduced onto Merck ®60 silica gel (70–230 mesh) (H: 30 cm; φ: 3 cm) and elution is carried out with ethyl acetate and then progressively with methanol. The eluate is fractionated, the pure fractions are evaporated, the residue is taken up in ether and the solid is filtered off and dried.

| Yield: | 120 mg (85%). |
|---|---|
| Aminoacid analysis: | Ala: 1.05 (1) |
| | Sta: 1.91 (2) |
| | Trp: 2.04 (2) |

NMR spectrum:

| δ | appearance | integration | assignment |
|---|---|---|---|
| 0.59–0.83 | m | 12 H | $^6C(CH_3)_2$ Sta |
| 0.91–1.57 | m | 18 H | $CH_3$ Ala / $^5CH_2$—$^6CH$ Sta / $(CH_3)_3C$ Boc |
| 2.03–2.38 | m | 4 H | $^2CH_2$ Sta |
| 2.56–3.23 | m | 4 H | $^3CH_2$ Trp |
| 3.50 | s | 3 H | $CH_3$ ester |
| 3.70–3.89 | m | 4 H | $^4CH$—$^3CH$ Sta |
| 4.05–4.24 | m | 2 H | $^2CH$ Ala |
| 4.41–4.54 | m | 1 H | 2 × $^2CH$ Trp |
| 4.75 | d | 2 H | 2 × OH Sta |
| 4.90 | d | | |
| 6.58 | d | 1 H | NH |
| 6.78–7.67 | m | 12 H | aromatic protons / 2 × NH |
| 7.81 | d | 1 H | NH |
| 8.03 | d | 1 H | NH |
| 10.69 | s | 1 H | NH indole |
| 10.74 | s | 1 H | NH indole |

EXAMPLE 8

Boc—Phe—His—Sta—Ala—Sta—OMe (SR 41395)

1. Boc—His(Boc)—Sta—OMe 0.8 g (0.0015 mol) of Boc—His(Boc)—OH.DCHA are solubilised in 80 ml of methylene chloride; 306 mg of H—Sta—OMe.TFA are added, the mixture is stirred until a solution is obtained, and 0.8 g of Bop and 233 mg of DIPEA are then added. The pH is monitored with time and adjusted to 6-7, if necessary, with DIPEA. After 24 hours, the solvent is evaporated off. The produce is dissolved in ethyl acetate and introduced into the top of column (L: 60 cm, φ: 3 cm) containing Merck ®60 silica gel (70–230 mesh) in ethyl acetate. Elution is carried out with ethyl acetate and the eluate is fractionated. The pure fractions are evaporated. The residue is taken up in hexane, the hexane is evaporated off and the solid obtained is dried.

Yield: 610 mg (77%).

2. Boc—Phe—His—Sta—OMe 350 mg of Boc—His(Boc)—Sta—OMe are covered with 5 ml of TFA at ambient temperature. After 30 minutes, the mixture is evaporated to dryness. The residue is dissolved in 50 ml of dioxane, 237 mg of NEM are then added and a check is made to ensure that the pH is 6-7; if not, it is adjusted. 89 mg of HOBt and 260 mg of Boc—Phe—ONSu are added. The pH is adjusted to 6-7, if necessary, with NEM. The mixture is stirred for 24 hours at AT and the solvent is evaporated off. The residue is dissolved in a 95/5 mixture of ethyl acetate and methanol and the solution is chromatographed on a column (L: 40 cm, φ: 2 cm) containing Merck ®60 silica gel (70–230 mesh) in the same solvent. Elution is carried out with 300 ml of the same solvent mixture and then with a 90/10 mixture of ethyl acetate and methanol; the eluate is fractionated and the pure fractions are evaporated.

Yield: 130 mg (34%).

3. Boc—Phe—His—Sta—OH 450 mg of Boc—Phe—His—Sta—OMe are solubilised in 20 ml of methanol. 5 ml of water are added, followed by 200 mg of powdered barium oxide. After 45 minutes, a further 100 mg of barium oxide are added. After 1 hour 30 minutes, the reaction is stopped; carbon dioxide is bubbled in for 30 minutes and the mixture is filtered on cellulose acetate; the latter is washed with methanol. The solvents are evaporated off; the residue is taken up in ether and the solid is filtered off and dried.

Yield: 400 mg.

4. Boc—Phe—His—Sta—Ala—Sta—OMe 180 mg of Boc—Ala—Sta—OMe are covered with 5 ml of TFA. After 30 minutes at ambient temperature, the solvent is evaporated off, ether is added and the solvent is evaporated off again. The oil is dissolved in 10 ml of DMF, and DIPEA is added until a pH of 6–7 to pH paper is obtained. 230 mg of Boc—Phe—His—Sta—OH in 10 ml of DMF containing 53 mg of DIPEA are then added, followed by a solution of 268 mg of Bop in 10 ml of DMF containing 76 mg of DIPEA; the mixture is stirred at AT and the pH is adjusted to 6–7, if necessary, with DIPEA. After 24 hours, the solvent is evaporated off to dryness under a high vacuum in a water-bath at 40°. The residue is taken up in water, extraction is carried out with methylene chloride and the organic solution is washed with water, $NaHCO_3$ solution and water. It is dried over $Na_2SO_4$, the solvent is then evaporated off and the residue is dissolved in a 2/98 mixture of methanol and chloroform and chromatographed on a column (L: 35 cm; φ: 2 cm) containing Merck ®60 silica gel (70–230 mesh) in the same solvent mixture. Elution is carried out with mixtures of methanol and $CHCl_3$ with a gradient up to 10/90. The eluate is fractionated and the pure fractions are evaporated. The residue is taken up in ether and the solid is filtered off and dried.

| Yield: | 150 mg (45%). |
|---|---|
| Aminoacid analysis: | Ala: 1.01 (1) |
| | Phe: 0.98 (1) |
| | His: 0.99 (1) |

NMR spectrum:

| δ | appearance | integration | assignment |
|---|---|---|---|
| 0.67–0.86 | m | 12 H | $^6(CH_3)_2$ Sta |
| 0.86–1.57 | m | 18 H | { $CH_3$ Ala / $(CH_3)_3C$ Boc / $^5CH_2—^6CH$ Sta |
| 1.97–2.38 | m | 4 H | $^2CH_2$Sta |
| 2.61–2.96 | m | 4 H | $^3CH_2$Phe, His |
| 3.50 | s | 3 H | $CH_3$ester |
| 3.65–3.87 | m | 4 H | $^4CH—^3CH$ Sta |
| 4.03–4.26 | m | 2 H | $^2CH$ Phe, Ala |
| 4.42 | m | 1 H | $^2CH$ His |
| 4.93 | m | 2 H | OH Sta |
| 6.77 | s | 1 H | $^4CH$ His |
| 6.98 | d | 1 H | NH |
| 7.08–7.27 | m | 5 H | aromatic protons |
| 7.33 | d | 2 H | NH |
| 7.38 | d | | NH |
| 7.52 | s | 1 H | $^2CH$ His |
| 7.96 | d | 1 H | NH |
| 8.14 | d | 1 H | NH |

EXAMPLE 9

Z—Phe—Val—Sta—Ala—Sta—OMe (SR 41405)

100 mg of H—Val—Sta—Ala—Sta—OMe.TFA (Example 6-2) are covered with 10 ml of dioxane containing 40 mg of NEM. 75 mg of Z—Phe—ONSu and 25.5 mg of HOBt are added. The mixture is stirred at ambient temperature and the pH is adjusted to 6–7, if necessary, with NEM. After 24 hour, the solvent is evaporated off and the residue is taken up in water. The solid is filtered off, washed with ether and dried.

| Yield: | 105 mg (81%). |
|---|---|
| Aminoacid analysis: | Ala: 1.00 (1) |
| | Val: 0.99 (1) |
| | Phe: 1.03 (1) |
| | Sta: 1.98 (2) |

NMR spectrum:

| δ | appearance | integration | assignment |
|---|---|---|---|
| 0.69–0.89 | m | 18 H | { $^6C(CH_3)_2$ Sta / $^3C(CH_3)_2$ Val |
| 1.07–1.57 | m | 9 H | { $^5CH_2—^6CH$ Sta / $CH_3$ Ala |
| 1.81–2.37 | m | 5 H | { $^3CH$ Val / $^2CH_2$ Sta |
| 2.58–2.98 | m | 2 H | $^3CH_2$ Phe |
| 3.50 | s | 3 H | $CH_3$ ester |
| 3.78 | m | 4 H | $^4CH—^3CH$ Sta |
| 4.06–4.34 | m | 3 H | $^2CH$ Phe, Val, Ala |
| 4.78 | d | | OH Sta |
| 4.86 | s | 4 H | $CH_2$ Z |
| 4.90 | d | | OH Sta |
| 7.00–7.34 | m | 11 H | aromatic protons |
| 7.42 | m | 2 H | { 1 NH / 2 NH |
| 7.79 | d | 1 H | NH |
| 7.87 | d | 1 H | NH |

EXAMPLE 10

Z—Phe—(D)Phe—Sta—Ala—Sta—OH (SR 41406)

110 mg of Z—Phe—(D)Phe—Sta—Ala—Sta—OMe (Example 3) are solubilised in 5 ml of DMF. 2 ml of water are added and 0.2 ml of normal sodium hydroxide solution (1.5 equivalents) is then added at AT. The mixture is stirred for 30 minutes at ambient temperature and 0.2 ml of normal hydrochloric acid is then added (the pH is then 6 to pH paper). The solvents are evaporated off under a high vacuum in a water-bath at 40°. The residue is taken up in water and triturated and the solid is filtered off and dried.

| Yield: 90 mg (83%). | | |
|---|---|---|
| Aminoacid analysis: | Ala | 0.91 (1) |
| | Phe | 2.00 (2) |
| | Sta | 2.03 (2) |

EXAMPLE 11

Z—Phe—(D)Trp—Sta—Ala—Sta—OMe (SR 41407)

80 mg of H—(D)Trp—Sta—Ala—Sta—OMe (Example 7) are covered with 10 ml of dioxane containing 27 mg of NEM, and 51 mg of Z-Phe-ONSu and 17 mg of HOBt are then added. The pH is adjusted to 6–7 to pH paper, if necessary, and the mixture is stirred at AT; after 24 hours, the solvent is evaporated off in vacuo, the residue is taken up in water, the solid is filtered off after one hour and then dissolved in methylene chloride and the organic solution is washed successively with $KHSO_4$-$K_2SO_4$ solution, water, $NaHCO_3$ solution and water. It is dried over $Na_2SO_4$ and the solvent is evaporated off. The product is dissolved in a 2/98 mixture of methanol and chloroform and introduced into the top of a column (L: 40 cm; φ: 2 cm) containing Merck ® 60 silica gel (70-230 mesh) in the same solvent mixture. Elution is carried out with 200 ml of a 2/98 mixture of methanol and chloroform and 400 ml of a 5/95 mixture of methanol and chloroform. The eluate is fractionated, TLC is carried out and the pure fractions are evaporated. The residue is taken up in ether and the solid is filtered off and dried.

| Yield: | 50 mg (51%). |
|---|---|
| Aminoacid analysis: | Ala: 1.01 (1) |
| | Phe: 1.01 (1) |
| | Sta: 1.99 (2) |
| | Trp: 1 (1) |

NMR spectrum:

| δ | appearance | integration | assignment |
|---|---|---|---|
| 0.64–0.86 | m | 12 H | $^6C(CH_3)_2$ Sta |
| 1.00–1.60 | m | 9 H | CH$_3$ Ala |
| | | | $^5CH_2$—$^6CH$ Sta |
| 2.10–2.42 | m | 4 H | $^2CH_2$ Sta |
| 2.48–3.20 | m | 4 H | $^3CH_2$ Phe, Trp |
| 3.50 | s | 3 H | CH$_3$ ester |
| 3.71–3.89 | m | 4 H | $^4CH$—$^3CH$ Sta |
| 4.13–4.26 | m | 2 H | $^2CH$ Phe, Ala |
| 4.51 | m | 1 H | $^2CH$ Trp |
| 4.75–4.95 | m | 4 H | 2 OH Sta |
| | | | $CH_2$ Z |
| 6.85–7.49 | m | 17 H | aromatic protons |
| | | | 2 NH |
| 7.60 | d | 1 H | NH |
| 7.84 | d | 1 H | NH |
| 8.24 | d | 1 H | NH |

EXAMPLE 12

Z Phe—Trp—Sta—Ala—Sta—OMe (SR 41416)

80 mg of H—Trp—Sta—Ala—Sta—OMe.TFA (Example 5) are solubilised in 20 ml of dioxane containing 27 mg of NEM, and 51 mg of Z—Phe—ONSu and 17 mg of HOBt are then added. The mixture is stirred at AT and the pH is adjusted to 6–7, if necessary, with NEM. After 48 hours, the solvent is evaporated off, the residue is taken up in water and the solid is filtered off and washed successively with $KHSO_4$-$K_2SO_4$ solution and then with water, $NaHCO_3$ solution and water. It is dissolved in ethyl acetate and the solution is dried over $MgSO_4$ and then evaporated to dryness. The residue is triturated in ether and the solid is filtered off and dried.

| Yield: | 90 mg (92%). |
|---|---|
| Aminoacid analysis: | Ala: 0.97 (1) |
| | Phe: 0.99 (1) |
| | Sta: 2.00 (2) |
| | Trp: 1.04 (1) |

NMR spectrum:

| δ | appearance | integration | assignment |
|---|---|---|---|
| 0.69–0.85 | m | 12 H | $^6C(CH_3)_2$ Sta |
| 1.09–1.58 | m | 9 H | CH$_3$ Ala |
| | | | $^5CH_2$—$^6CH$ Sta |
| 1.90–2.4 | m | 4 H | $^2CH_2$ Sta |
| 2.53–3.20 | m | 4 H | $^3CH_2$ Phe, Trp |
| 3.50 | s | 3 H | CH$_3$ ester |
| 3.79 | m | 4 H | $^4CH$—$^3CH$ Sta |
| 4.11–4.27 | m | 2 H | $^2CH$ Phe, Ala |
| 4.51 | m | 1 H | $^2CH$ Trp |
| | | | 2 OH Sta |
| 4.75–5.00 | m | 4 H | |
| | | | $CH_2$ Z |
| 6.86–7.50 | m | 17 H | aromatic protons |
| | | | 2 NH |
| 7.57 | d | 1 H | NH |
| 7.79 | d | 1 H | NH |
| 8.19 | d | 1 H | NH |
| 10.69 | s | 1 H | NH indole |

EXAMPLE 13

Z—Tyr—Val—Sta—Ala—Sta—OMe (SR 41476)

100 mg of H—Val—Sta—Ala—Sta—OMe.TFA (Example 6-2) are covered with 10 ml of dioxane containing 45 mg of NEM. 82.5 mg of Z—Tyr—ONSu and 27.5 mg of HOBt are added. The pH is adjusted to 6–7, if necessary, with NEM. The mixture is stirred for 48 hours at ambient temperature. The solvent is evaporated off in the cold, the residue is taken up in water and the white solid obtained is filtered off, washed with water and dried. It is washed with ether and dried.

| Yield: | 110 mg (85%). |
|---|---|
| Aminoacid analysis: | Ala: 1.02 (1) |
| | Val: 0.99 (1) |
| | Tyr: 0.99 (1) |
| | Sta: 2.01 (2) |

NMR spectrum:

| δ | appearance | integration | assignment |
|---|---|---|---|
| 0.69–0.88 | m | 18 H | $^6C(CH_3)_2$ Sta |
| | | | $^3C(CH_3)_2$ Val |
| 1.09–1.58 | m | 9 H | CH$_3$ Ala |
| | | | $^5CH_2$—$^6CH$ Sta |
| 1.82–2.00 | m | 1 H | $^3CH$ Val |
| 2.00–2.40 | m | 4 H | $^2CH_2$ Sta |
| 2.50–2.88 | m | 2 H | $^3CH_2$ Tyr |
| 3.50 | s | 3 H | CH$_3$ ester |
| 3.70–3.86 | m | 4 H | $^4CH$—$^3CH$ Sta |
| 4.06–4.27 | m | 3 H | $^2CH$ Tyr, Val, Ala |
| 4.80 | d | | OH Sta |
| 4.88 | s | 4 H | $CH_2$ Z |
| 4.91 | d | | OH Sta |
| 6.58 | d | 2 H | 3',5'CH aromatic Tyr |
| 7.00 | d | 2 H | 2',6'CH aromatic Tyr |
| 7.09–7.50 | m | 8 H | aromatic protons Z |
| | | | 3 × NH |
| 7.77–7.90 | m | 2 H | 2 × NH |

EXAMPLE 14

Z—Phe—ILe—Sta—Ala—Sta—OMe (SR 41477)

1. Boc—Ile—Sta—Ala—Sta—OMe 265 mg of H—Sta—Ala—Sta—OMe.TFA (Example 1-4) are covered with 30 ml of dioxane containing 206 mg of DIPEA. 125 mg of BOC—Ile—OH at 270 mg of Bop are added. The pH is adjusted to 6-7, if necessary, with DIPEA and the mixture is stirred for 48 hours at AT. The solvent is evaporated off in vacuo, the residue is taken up in ether and the solid is filtered off. A solution of the product in 2.5/97.5 mixture of methanol and chloroform is introduced into the top of a column (L: 30 cm; φ: 2 cm) containing Merck$^R$ 60 silica gel (70-230 mesh) in the same solvent. Elution is carried out with the same solvent mixture (250 ml) and then with 200 ml of a 5/95 mixture of methanol and chloroform and 200 ml of a 7.5/92.5 mixture of methanol and chloroform. The eluate is fractionated, the pure fractions are evaporated, the residue is taken up in ether and the solid is filtered off and dried.

Yield: 180 mg (56%).

2. H—Ile—Sta—Ala—Sta—OMe.TFA 150 mg of Boc—Ile—Sta—Ala—Sta—OMe are covered with 2 ml of TFA. After 30 minutes, the solvent is evaporated off, the residue is taken up in ether and the white solid is filtered off, washed with ether and dried. Yield: 140 mg (93%).

3. Z—Phe—Ile—Sta—Ala—Sta—OMe (SR 41477)

126 mg of H—Ile—Sta—Ala—Sta—OMe.TFA are covered with 20 ml of dioxane containing 51 mg of NEM. 95 mg of Z—Phe—ONSu and 32 mg of HOBt are added. The pH is adjusted to 6-7, if necessary, with NEM, the mixture is stirred for 48 hours at AT and the solvent is evaporated off in vacuo. The residue is taken up in water and triturated and the solid is filtered off and dried. It is washed with ether and dried.

| Yield: | | 140 mg (86%). | |
|---|---|---|---|
| Aminoacid analysis: | | Ala: 0.96 (1) | |
| | | Ile: 0.98 (1) | |
| | | Phe: 1.03 (1) | |
| | | Sta: 2.03 (2) | |
| NMR spectrum: | | | |
| δ | appearance | integration | assignment |
| 0.64-0.91 | m | 18 H | $^6$C(CH$_3$)$_2$ Sta |
| | | | $^3$CH$_3$ $^4$CH$_3$ Ile |
| 0.91-1.81 | m | 12 H | CH$_3$ Ala |
| | | | $^5$CH$_2$—$^6$CH Sta |
| | | | $^4$CH$_2$—$^3$CH Ile |
| 2.00-2.39 | m | 4 H | $^2$CH$_2$ Sta |
| 2.50-2.96 | m | 2 H | $^3$CH$_2$ Phe |
| 3.50 | s | 3 H | CH$_3$ ester |
| 3.79 | m | 4 H | $^4$CH—$^3$CH Sta |
| 4.08-4.35 | m | 3 H | $^2$CH Phe, Ile, Ala |
| 4.80 | d | | OH Sta |
| 4.88 | s | 4 H | CH$_2$ Z |
| 4.93 | d | | OH Sta |
| 7.09-7.36 | m | 11 H | aromatic protons + 1 NH |
| 7.44 | 2 d | 2 H | 2 NH |
| 7.79 | d | 1 H | NH |
| 7.94 | d | 1 H | NH |

EXAMPLE 15

Z—Phe—(D)Val—Sta—Ala—Sta—OMe (SR 41478)

1. Boc—(D)Val—Sta—Ala—Sta—OMe 531 mg of H—Sta—Ala—Sta—OMe.TFA (Example 1-4) are covered with 50 mg of dioxane containing 253 mg of NEM; 380 mg of Boc—(D)Val—ONSu and 135 mg of HOBt are then added. The pH is adjusted to 6-7, if necessary, with NEM and the mixture is stirred for 3 days at AT; the solvent is evaporated off in vacuo, the residue is taken up in water and extraction is carried out with methylene chloride. The organic phase is washed with water and dried over Na$_2$SO$_4$ and the solvent is evaporated off. The residue is taken up in ether and the mixture is left to stand. The white precipitate formed is filtered off in vacuo and dried.

Yield: 250 mg (40%).

2. H—(D)Val—Sta—Ala—Sta—OMe.TFA 150 mg of Boc—(D)Val—Sta—Ala—Sta—OMe are covered with 2 ml of TFA. After 30 minutes at ambient temperature, the solvent is evaporated off to dryness. The residue is taken up in ether and the solid obtained is filtered off in vacuo, washed with ether and dried.

Yield: 150 mg (100%).

3. Z—Phe—(D)Val—Sta—Ala—Sta—OMe 100 mg of H—(D)Val—Sta—Ala—Sta—OMe.TFA and then 75 mg of Z—Phe—ONSu and 25.5 mg of HOBt are introduced successively into 25 ml of dioxane containing 40 mg of NEM. The mixture is stirred at AT. 3 days after the pH has been adjusted to 6-7, if necessary, the solvent is evaporated off in vacuo and the residue is washed with water and then with ether and dried.

| Yield: | | 80 mg (29%). | |
|---|---|---|---|
| Aminoacid analysis: | | Ala: 0.97 (1) | |
| | | Val: 1.03 (1) | |
| | | Phe: 1.01 (1) | |
| | | Sta: 1.98 (2) | |
| NMR spectrum: | | | |
| δ | appearance | integration | assignment |
| 0.62-0.85 | m | 18 H | $^6$C(CH$_3$)$_2$ Sta |
| | | | $^3$C(CH$_3$)$_2$ Val |
| 1.06-1.57 | m | 9 H | $^5$CH$_2$—$^6$CH Sta |
| | | | CH$_3$ Ala |
| 1.92 | m | 1 H | $^3$CH Val |
| 2.06-2.35 | m | 4 H | $^2$CH$_2$ Sta |
| 2.50-3.00 | m | 2 H | $^3$CH$_2$ Phe |
| 3.51 | s | 3 H | CH$_3$ ester |
| 3.77 | m | 4 H | $^4$CH—$^3$CH Sta |
| 4.10-4.38 | m | 3 H | $^2$CH Phe, (D)Val, Ala |
| 4.72-4.94 | m | 4 H | 2 OH Sta |
| | | | CH$_2$ Z |
| 7.04-7.92 | m | 15 H | aromatic protons |
| | | | 5 × NH |

EXAMPLE 16

Z—Trp—Val—Sta—Ala—Sta—OMe (SR 41485)

70 mg of H—Val—Sta—Ala—Sta—OMe.TFA (Example 6) are covered with 20 ml of dioxane containing 30 mg of NEM. 67 mg of Z—Trp—ONp and 20 mg of HOBt are added at AT. The pH is adjusted to 6-7, if necessary, with NEM and the mixture is stirred at AT; after 48 hours, the solvent is evaporated off in vacuo, the oily residue is taken up in water, the water is decanted and the residue is taken up in ether. The solid obtained is filtered off, washed with ether and dried.

| Yield: | 40 mg. | |
|---|---|---|
| Aminoacid analysis: | Ala: 1.01 | (1) |

|   |   |   |   |
|---|---|---|---|
|   | Val: 1 | (1) |   |
|   | Sta: 2.03 | (2) |   |
|   | Trp: 0.95 | (1) |   |

| NMR spectrum: | | | |
|---|---|---|---|
| δ | appearance | integration | assignment |
| 0.71–0.93 | m | 18 H | $^6C(CH_3)_2$ Sta<br>$^3C(CH_3)_2$ Val |
| 1.09–1.62 | m | 9 H | $CH_3$ Ala<br>$^5CH_2$—$^6CH$ Sta |
| 1.87–2.40 | m | 5 H | $^3CH$ Val<br>$^2CH_2$ Sta |
| 3.50 | s | 3 H | $CH_3$ ester |
| 3.71–3.89 | m | 4 H | $^4CH$—$^3CH$ Sta |
| 4.05–4.43 | m | 3 H | $^2CH$ Trp, Val, Ala |
| 4.77–5.00 | m | 4 H | 2 OH Sta<br>$CH_2$ Z |
| 6.83–8.00 | m | 15 H | aromatic protons<br>5 × NH |
| 10.72 | s | 1 H | NH Indole |

EXAMPLE 17

Boc—(D)Phe—Val—Sta—Ala—Sta—OH (SR 41491)

76 mg of Boc—(D)Phe—Val—Sta—Ala—Sta—OMe (Example 6) are solubilised in 4 ml of DMF; 1 ml of water is added and 0.15 ml of normal sodium hydroxide solution is then added at AT. The mixture is stirred for 40 minutes at AT and 0.15 ml of normal hydrochloric acid is then added. The solvents are evaporated off under a high vacuum in a water-bath at 35° C. The residue is taken up in water. The solid is filtered off and dried. It is washed with ether and dried.

| Aminoacid analysis | Ala | 0.98 (1) |
|---|---|---|
|   | Val | 0.96 (1) |
|   | Phe | 0.97 (1) |
|   | Sta | 2.05 (2) |

EXAMPLE 18

Boc—Phe—His—Sta—Ala—Sta—OH (SR 41492)

60 mg of Boc—Phe—His—Sta—Ala—Sta—OMe (Example 8) are solubilised in 4 ml of DMF; 1 ml of water is added and 0.12 ml of normal sodium hydroxide solution is then added at AT. The mixture is stirred for 40 minutes at AT and 0.12 ml of normal hydrochloric acid is then added. The solvents are evaporated off under a high vacuum in a water-bath at 35°. The residue is taken up in water and the solid obtained is filtered off and dried.

| Yield: 30 mg. | | |
|---|---|---|
| Aminoacid analysis: | Ala | 1.01 (1) |
|   | Phe | 1.01 (1) |
|   | His | 0.96 (1) |
|   | Sta | 2.02 (2) |

EXAMPLE 19

Boc—(D)Phe—Phe—Sta—Ala—Sta—OMe (SR 41518)

150 mg of H—Phe—Sta—Ala—Sta—OMe.TFA (Example 1) and 37 mg of HOBt are covered with 30 ml of dioxane containing 57 mg of NEM. 98 mg of Boc—(D)Phe—ONSu are added and the mixture is stirred at AT. The pH is monitored and adjusted to 6–7, if necessary, with NEM. After 48 hours, the solvent is evaporated off, the residue is taken up in water and the white solid obtained is filtered off, washed with water and then with ether and dried.

| Yield: | 150 mg (82%). |
|---|---|
| Aminoacid analysis: | Ala: 1.0 (1) |
|   | Phe: 1.92 (2) |
|   | Sta: 2.07 (2) |

| NMR spectrum: | | | |
|---|---|---|---|
| δ | appearance | integration | assignment |
| 0.71–0.86 | m | 12 H | $^6C(CH_3)_2$ Sta |
| 1.07–1.59 | m | 18 H | $CH_3$ Ala<br>$(CH_3)_3C$ Boc<br>$^5CH_2$—$^6CH$ Sta |
| 1.97–2.37 | m | 4 H | $^2CH_2$ Sta |
| 2.37–2.62 | m | * | $^3CH_2$ (D)Phe |
| 2.65–3.06 | m | 2 H | $^3CH_2$ Phe |
| 3.50 | s | 3 H | $CH_3$ ester |
| 3.67–3.90 | m | 4 H | $^4CH$—$^3CH$ Sta |
| 4.02–4.15 | m |  | $^2CH$ (D)Phe |
|   |   | 2 H | $^2CH$ Ala |
| 4.15–4.28 | m |  |   |
| 4.46–4.60 | m | 1 H | $^2CH$ Phe |
| 4.76 | d | 1 H | 2 × OH Sta |
| 4.92 | d | 1 H |  |
| 6.58 | d | 1 H | NH (D)Phe |
| 6.96–7.25 | m | 10 H | aromatic protons |
| 7.31 | d | 1 H | 2 × NH Sta |
| 7.45 | d | 1 H |  |
| 7.80 | d | 1 H | NH Ala |
| 8.16 | d | 1 H | NH Phe |

*integration impossible because of the DMSO peak at δ = 2.45

EXAMPLE 20

Adoc—Phe—Phe—Sta—Ala—Sta—OMe (SR 41540)

221 mg of H—Phe—Sta—Ala—Sta—OMe.TFA (Example 1) and 54 mg of HOBt are covered with 30 ml of dioxane containing 84 mg of NEM. 175 mg of Adoc—Phe—ONSu are added. The mixture is stirred at ambient temperature. The pH is monitored and adjusted to 6–7, if necessary, with NEM. After 48 hours, the solvent is evaporated off in vacuo, the residue is taken up in water and the solid is filtered off and dried. A solution of the product in a 1/99 mixture of methanol and chloroform is introduced into the top of a column containing Merck ®60 silica gel (70–230 mesh) in the same solvent (L: 40 cm; φ: 2 cm). Elution is carried out with 200 ml of a 1/99 mixture of methanol and chloroform, 300 ml of a 2/98 mixture of methanol and chloroform and 300 ml of a 5/95 mixture of methanol and chloroform. The eluate is fractionated and the pure fractions are evaporated. The residue is taken up in ether and the solid is filtered off and dried.

| Yield: | 170 mg (58%). |
|---|---|
| Aminoacid analysis: | Ala: 1.05 (1) |
|   | Sta: 1.97 (2) |

|  |  | -continued |  |
|---|---|---|---|
|  |  | Phe: 2.04 (2) |  |
|  | NMR spectrum: |  |  |
| δ | appearance | integration | assignment |
| 0.71–0.91 | m | 12 H | $^6C(CH_3)_2$ Sta |
| 1.09–2.03 | m | 24 H | CH$_3$ Ala<br>$^5CH_2$—$^6$CH Sta<br>CH$_2$ and CH Adoc |
| 2.08–2.37 | m | — | $^2CH_2$ Sta |
| 2.56–3.06 | m | — | $^3CH_2$ Phe |
| 3.50 | s | — | CH$_3$ ester |
| 3.68–3.87 | m | 4H | $^4$CH—$^3$CH Sta |
| 3.94–4.58 | m | 3 H | $^2$CH Phe, Ala |
| 4.78 | d | } — | OH Sta |
| 4.93 | d |  |  |
| 6.86 | d | 1 H | NH |
| 7.06–7.26 | m | 10 H | aromatic protons |
| 7.34 | d | 1 H | NH |
| 7.52 | d | 1 H | NH |
| 7.78 | d | 1 H | NH |
| 7.94 | d | 1 H | NH |

EXAMPLE 21

Boc—His(Boc)—Phe—Sta—Ala—Sta—OMe (SR 41541)

100 mg of H—Phe—Sta—Ala—Sta—OMe (Example 1) and 75 mg of Boc—His(Boc)—OH.DCHA are solubilised in 20 ml of dioxane containing 10 ml of DMF. 72 mg of Bop and 20.6 mg of DIPEA are added. The mixture is stirred at AT and the pH is adjusted to 6–7, if necessary, with DIPEA. After 48 hours, the solvents are evaporated off in a water-bath at 35° under a high vacuum. The residue is taken up in water and extraction is carried out with methylene chloride. The organic phase is dried over Na$_2$SO$_4$. The solvent is evaporated off. The residue is dissolved in chloroform and introduced into the top of a column (L: 40 cm; φ: 2 cm) containing Merck ®60 silica gel (70–230 mesh) in chloroform. Elution is carried out with 200 ml of chloroform, 200 ml of a 1/99 mixture of methanol and chloroform, 200 ml of a 2/98 mixture of methanol and chloroform, 100 ml of a 3/97 mixture of methanol and chloroform and 300 ml of a 4/96 mixture of methanol and chloroform. The eluate is fractionated. The pure fractions are evaporated. The residue is taken up in a 50/50 mixture of ether and hexane and the solid is filtered off and dried.

| Yield: | 70 mg (60%). |
|---|---|
| Aminoacid analysis: | Ala: 0.91 (1) |
|  | His: 1.20 (1) |
|  | Phe: 1.05 (1) |
|  | Sta: 1.80 (2) |

|  | NMR spectrum: |  |  |
|---|---|---|---|
| δ | appearance | integration | assignment |
| 0.69–0.83 | m | 12 H | $^6C(CH_3)_2$ Sta<br>CH$_3$ Ala |
| 1.09–1.54 | m | 27 H | (CH$_3$)$_3$C diBoc<br>$^5CH_2$—$^6$CH Sta |
| 1.94–2.37 | m | 4 H | $^2CH_2$ Sta |
| 2.50–3.02 | m | 4 H | $^3CH_2$ Phe, His |
| 3.50 | s | — | $^4$CH—$^3$CH Sta |
| 3.68–3.87 | m | 4 H | $^4$CH—$^3$CH Sta |
| 4.00–4.26 | m | 2 H | } $^2$CH Phe, Ala, His |
| 4.43–4.59 | m | 1 H |  |
| 4.78 | d | } — | 2 × OH Sta |
| 4.93 | d |  |  |
| 6.85 | d | 1 H | NH |
| 7.06–7.22 | m | 6 H | aromatic protons<br>Phe<br>$^4$'CH His |
| 7.36 | d | 1 H | NH |
| 7.58 | d | 1 H | NH |
| 7.81 | d | 1 H | NH |
| 7.88 | d | 1 H | NH |
| 8.03 | s | 1 H | $^2$'CH His |

EXAMPLE 22

Z—Tyr—Tyr—Sta—Ala—Sta—OMe (SR 41542)

1. Z—Tyr—Sta—Ala—Sta—OMe 400 mg of H—Sta—Ala—Sta—OMe.TFA and then 310 mg of Z—Tyr—ONSu and 101 mg of HOBt are introduced successively into 25 ml of dioxide containing 244 mg of NEM. The mixture is stirred at AT and the pH is adjusted to 6–7, if necessary, with NEM. After 3 days, the solvent is evaporated off in a water-bath at 40° under a waterpump vacuum. The residue is taken up in water and the water is decanted. The residue is taken up in methylene chloride and the solid obtained is filtered off, washed with a 2/98 mixture of methanol and chloroform and dried.

Yield: 340 mg (75%).

2. H—Tyr—Sta—Ala—Sta—OMe 180 mg of Z—Tyr—Sta—Ala—Sta—OMe are dissolved in 50 ml of methanol. 40 mg of 10% strength Pd/C are added and the mixture is hydrogenated under a pressure of one meter of water. After one night, the mixture is filtered, the charcoal is washed with methanol, the solvent is evaporated off, the residue is taken up in ether and the mixture is evaporated to dryness. The residue is taken up in ether, precipitation is induced by scratching and the solid obtained is filtered off and dried.

Yield: 110 mg (96%).

3. Z—Tyr—Tyr—Sta—Ala—Sta—OMe 100 mg of H—Tyr—Sta—Ala—Sta—OMe, 82 mg of Z—Tyr—ONSu and 27 mg of HOBt are solubilised in 30 ml of dioxane containing 23 mg of NEM. The mixture is stirred at AT. The pH is adjusted to 6–7, if necessary, with NEM. After 48 hours, the solvent is evaporated off and the residue is taken up in water and triturated. After 30 minutes, the solid obtained is filtered off, washed with water and dried. It is washed with ether and then with methylene chloride. It is dissolved in methanol, the solution is filtered, the solvent is evaporated off, the residue is concentrated and a solid is precipitated with ether, filtered off and dried.

| Yield: | 100 mg (71%). |
|---|---|
| Aminoacid analysis: | Ala: 1.03 (1) |
|  | Tyr: 1.92 (2) |
|  | Sta: 2.02 (2) |

|  | NMR spectrum: |  |  |
|---|---|---|---|
| δ | appearance | integration | assignment |
| 0.70–0.86 | m | 12 H | $^6C(CH_3)_2$ Sta<br>CH$_3$ Ala |
| 1.12–1.60 | m | 9 H | $^5CH_2$—$^6$CH Sta |
| 1.95–2.37 | m | 4 H | $^2CH_2$ Sta |
| 2.48–2.94 | m | 4 H | $^3CH_2$ Tyr |
| 3.50 | s | — | CH$_3$ ester |
| 3.70–3.89 | m | 4 H | $^4$CH—$^3$CH Sta |
| 4.00–4.48 | m | 3 H | $^2$CH Tyr, Ala<br>2 × OH Sta |

| | | | |
|---|---|---|---|
| 4.75–4.96 | m | 4 H | CH$_2$ Z |
| 6.51–6.63 | 2 d | 4 H | 3',5'CH Tyr |
| 6.90–7.07 | 2 d | 4 H | 2',6'CH Tyr |
| 7.14–7.50 | m | 8 H | aromatic protons Z, 3 × NH |
| 7.81 | d | 1 H | NH |
| 8.00 | d | 1 H | NH |
| 9.06 | s | — | 4'OH Tyr |
| 9.10 | s | | |

EXAMPLE 23

Boc—Pro—Pro—Sta—Ala—Sta—OMe (SR 41543)

1. Boc—Pro—Sta—Ala—Sta—OMe 630 mg of H—Sta—Ala—Sta—OMe.TFA (Example 1-4) and then 374 mg of Boc—Pro—ONSu and 162 mg of HOBt are added successively to 70 ml of dioxane containing 253 mg of NEM. The mixture is stirred at AT. The pH is adjusted to 6–7, if necessary, with NEM. After 48 hours, the solvent is evaporated off in vacuo and the residue is taken up in water. Extraction is carried out with methylene chloride. The extract is dried over Na$_2$SO$_4$ and the solvent is evaporated off. The residue is dissolved in chloroform and introduced into the top of a column (L: 40 cm; φ: 2 cm) containing Merck®60 silica gel (70–230 mesh) in chloroform. Elution is carried out with 200 ml of chloroform, 300 ml of a 1/99 mixture of methanol and chloroform, 100 ml of a 2/98 mixture of methanol and chloroform, 100 ml of a 3/97 mixture of methanol and chloroform, 200 ml of a 4/96 mixture of methanol and chloroform and 200 ml of a 5/95 mixture of methanol and chloroform. The eluate is fractionated. The pure fractions are evaporated. The residue is taken up in hexane. The solid is filtered off and dried.

Yield: 530 mg (85%).

2. H—Pro—Sta—Ala—Sta—OMe 500 mg of Boc—Pro—Sta—Ala—Sta—OMe are covered with 8 ml of TFA. After 30 minutes at AT, the solvent is evaporated off, the residue is taken up in ether and triturated, hexane is added and the solid is filtered off and dried.

Yield: 510 mg (100%).

3. Boc—Pro—Pro—Sta—Ala—Sta—OMe (SR 41543)

125 mg of H—Pro—Sta—Ala—Sta—OMe.TFA are covered with 35 ml of dioxane containing 48 mg of NEM. 69 mg of Boc—Pro—ONSu and 30 mg of HOBt are added. The mixture is stirred at AT. The pH is adjusted to 6–7, if necessary, with NEM. After 48 hours, the solvent is evaporated off in vacuo, the residue is taken up in water and extraction is carried out with methylene chloride. The organic phase is dried over Na$_2$SO$_4$ and evaporated to dryness. The residue is dissolved in chloroform and introduced into the top of a column (L: 40 cm; φ: 2 cm) containing Merck®60 silica gel (70–230 mesh) in chloroform. Elution is carried out with 200 ml of chloroform, 200 ml of a 1/99 mixture of methanol and chloroform, 200 ml of a 2/98 mixture of methanol and chloroform, 200 ml of a 3/97 mixture of methanol and chloroform and 300 ml of a 5/95 mixture of methanol and chloroform. The eluate is fractionated, the pure fractions are evaporated, the residue is taken up in ether and the ether is evaporated off to dryness.

| Yield: | 30 mg. |
|---|---|
| Aminoacid analysis: | Ala: 1 (1) |
| | Pro: 1.54 (2) |
| | Sta: 2.12 (2) |

NMR spectrum:

| δ | appearance | integration | assignment | |
|---|---|---|---|---|
| 0.69–0.85 | m | 12 H | 6C(CH$_3$)$_2$ | Sta |
| 1.09–2.35 | m | 30 H | CH$_3$ | Ala |
| | | | 5CH$_2$—6CH | Sta |
| | | | (CH$_3$)$_3$C | Boc |
| | | | β and γ CH$_2$ | Pro |
| | | | 2CH$_2$ | Sta |
| 3.18–3.65 | m | — | CH$_2$ | Pro |
| | | | 8CH$_3$ | ester |
| 3.65–3.89 | m | 4 H | 4CH—3CH | Sta |
| 4.08–4.21 | m | 1 H | 2CH | Ala |
| 4.29–4.40 | m | 2 H | 2CH | Pro |
| 4.72 | d | 1 H | OH | Sta |
| 4.86 | d | 1 H | OH | Sta |
| 7.30 | 2 d | 2 H | 2 × NH | Sta, Ala |
| 7.86 | d | 1 H | NH | |

EXAMPLE 24

Adoc—Phe—Trp—Sta—Ala—Sta—OMe (SR 41581)

143 mg of H—Trp—Sta—Ala—Sta—OMe.TFA (Example 5) are covered with 30 ml of dioxane containing 49 mg of NEM. 97 mg of Adoc—Phe—ONSu and 30 mg of HOBt are added. The pH is adjusted to 6–7, if necessary, with NEM and the mixture is stirred at AT. After 48 hours, the solvent is evaporated off, the residue is taken up in water and triturated and the solid is filtered off. The product is dissolved in chloroform and introduced into the top of a column (L: 60 cm: φ: 2 cm) containing Merck®60 silica gel (70–230 mesh) in chloroform. Elution is carried out with 200 ml of chloroform, 200 ml of a 1/99 mixture of methanol and chloroform, 200 ml of a 3/97 mixture of methanol and chloroform and 200 ml of a 5/95 mixture of methanol and chloroform. The pure fractions are evaporated, the residue is taken up in ether and the solid is filtered off and dried.

| Yield: | 120 mg (65%). |
|---|---|
| Aminoacid analysis: | Ala: 0.95 (1) |
| | Trp: 0.75 (1) |
| | Phe: 0.99 (1) |
| | Sta: 2.05 (2) |

NMR spectrum:

| δ | appearance | integration | assignment |
|---|---|---|---|
| 0.70–0.85 | m | 12 H | 6C—(CH$_3$)$_2$ Sta |
| | | | CH$_3$ Ala |
| | | | 5CH$_2$—6CH Sta |
| 1.14–2.42 | m | 28 H | CH$_2$ and CH Adoc |
| | | | 2CH$_2$ Sta |
| 2.50–3.20 | m | | 3CH$_2$ Phe, Trp |
| 3.50 | s | | CH$_3$ ester |
| 3.73–3.92 | m | 4 H | 4CH—3CH Sta |
| 3.95–4.61 | m | 3 H | 2CH Phe, Trp, Ala |
| 4.61 | d | — | OH Sta |
| 4.96 | d | | |
| 6.83–7.31 | m | 10 H | aromatic protons |
| 7.41 | d | 1 H | NH |
| 7.46 | d | 1 H | NH |
| 7.57 | d | 1 H | NH |
| 7.81 | d | 1 H | NH |

-continued

| | | | |
|---|---|---|---|
| 7.94 | d | 1 H | NH |
| 10.64 | s | 1 H | NH indole |

EXAMPLE 25

Z—Phe—Pro—Sta—Ala—Sta—OMe (SR 41603)

150 mg of H—Pro—Sta—Ala—Sta—OMe.TFA (Example 23-2) are covered with 20 ml of dioxane containing 59 mg of NEM, and 110 mg of Z—Phe—ONSu and 37 mg of HOBt are then added. The pH is adjusted to 6–7, if necessary, with NEM and the mixture is stirred for 48 hours at AT. After 48 hours, the solvent is evaporated off, the residue is taken up in water and extraction is carried out with methylene chloride. The extract is dried over $Na_2SO_4$, the solvent is evaporated off and the residue is then dissolved in chloroform and introduced into the top of a column (L: 60 cm; $\phi$: 2 cm) containing Merck ®60 silica gel (70–230 mesh) in chloroform. Elution is carried out with 200 ml of chloroform, 200 ml of a 1/99 mixture of methanol and chloroform, 200 ml of a 3/97 mixture of methanol and chloroform and 300 ml of a 5/95 mixture of methanol and chloroform. The fractions containing the product are evaporated.

Yield: 100 mg (54%).

NMR spectrum:

| δ | appearance | integration | assignment |
|---|---|---|---|
| 0.66–0.85 | m | 12 H | $^6$C(CH$_3$)$_2$ Sta |
| | | | CH$_3$ Ala |
| | | | $^5$CH$_2$—$^6$CH Sta |
| 1.09–2.35 | m | 17 H | β and γ CH$_2$ Pro |
| | | | $^2$CH$_2$ Sta |
| 2.50–3.02 | m | 2 H | $^3$CH$_2$ Phe |
| | | | δ CH$_2$ Pro |
| 3.20–3.65 | m | — | CH$_3$ ester |
| 3.66–3.86 | m | 4 H | $^4$CH—$^3$CH Sta |
| 4.06–4.42 | m | 3 H | $^2$CH Phe, Pro, Ala |
| 4.72–4.93 | m | 4 H | 2 OH Sta |
| | | | CH$_2$ Z |
| 7.09–7.44 | | 12 H | 10 aromatic protons |
| | | | 2 × NH |
| 7.63 | d | 1 H | NH |
| 7.88 | d | 1 H | NH |

EXAMPLE 26

Boc—(D)Trp—Trp—Sta—Ala—Sta—OMe (SR 41604)

120 mg of H—Trp—Sta—Ala—Sta—OMe.TFA (Example 5) are covered with 10 ml of dioxane containing 41 mg of NEM. 85 mg of Boc—(D)Trp—ONp and 27 mg of HOBt are added. The pH is adjusted to 6–7, if necessary, with NEM and the mixture is stirred for 48 hours at AT. The solvent is evaporated off, water is added, extraction is carried out with methylene chloride and the extract is dried over $Na_2SO_4$ and evaporated; the residue is dissolved in chloroform and introduced into the top of a column (L: 60 cm; $\phi$: 2 cm) containing Merck ®60 silica gel (70–230 mesh) in chloroform. Elution is carried out with 200 ml of chloroform, 200 ml of a 1/99 mixture of methanol and chloroform, 200 ml of a 2/98 mixture of methanol and chloroform, 200 ml of a 3/97 mixture of methanol and chloroform, 200 ml of a 4/96 mixture of methanol and chloroform and 300 ml of a 5/95 mixture of methanol and chloroform. The eluate is fractionated. The fractions containing the product are evaporated and the residue is taken up in ether. The solid is filtered off and dried.

Yield: 60 mg (42%).
Aminoacid analysis: Ala: 0.99 (1)
Trp: 1.97 (2)
Sta: 2.04 (2)

NMR spectrum:

| δ | appearance | integration | assignment |
|---|---|---|---|
| 0.72–0.92 | m | 12 H | $^6$C—(CH$_3$)$_2$ Sta |
| | | | CH$_3$ Ala |
| | | | $^5$CH$_2$—$^6$CH Sta |
| 1.12–1.60 | m | 18 H | |
| | | | (CH$_3$)$_3$C Boc |
| 2.00–2.38 | m | 4 H | $^2$CH$_2$ Sta |
| 2.50–3.15 | m | — | $^3$CH$_2$ Trp |
| 3.50 | s | — | CH$_3$ ester |
| 3.73–3.91 | m | 4 H | $^4$CH—$^3$CH Sta |
| | | | $^2$CH Ala |
| 4.08–4.59 | m | 3 H | |
| | | | 2 × $^2$CH Trp |
| 4.72 | d | | |
| | | | 2 × OH Sta |
| 4.93 | d | 2 H | |
| 6.54 | d | 1 H | NH |
| | | | aromatic protons |
| 6.80–7.47 | m | 11 H | |
| | | | 1 NH |
| 7.57 | d | 1 H | NH |
| 7.84 | d | 1 H | NH |
| 8.08 | d | 1 H | NH |
| 10.66 | s | 2 H | 2 × NH indole |

EXAMPLE 27

Boc—Trp—His—Sta—Ala—Sta—OMe (SR 41619)

1. Boc—His—Sta—OH 2.63 g of Boc—His(Boc)—Sta—OMe (Example 8-1) are solubilised in 200 ml of DMF containing 40 ml of water. With the temperature at 25°, 3.15 g of finely powdered barium oxide are added. The mixture is stirred and 150 ml of cold water are added gradually in order to prevent an increase in temperature. After 1 hour 30 minutes at AT, carbon dioxide is bubbled in, the mixture is then filtered and the solvents are evaporated off under a high vacuum in a water-bath at 40°. The residue is dissolved in methanol, the solution is filtered, the filtrate is concentrated and the residue is poured into ether to give a gel, which is filtered off with difficulty and dried.

Yield: 1.23 g (60%)

2. Boc—His—Sta—Ala—Sta—Ome 360 mg of Boc—Ala—Sta—OMe (Example 1) are covered with 3 ml of TFA. After 30 minutes at AT, the solvent is evaporated off and the residual oil is dissolved in DMF; DIPEA is added until a pH of 7–8 to pH paper is obtained, and 412 mg of Boc—His—Sta—OH and 672 mg of Bop are then added. The pH is adjusted to 6–7, if necessary, with DIPEA and the mixture is stirred for 48 hours at AT. The solvent is evaporated off under a high vacuum in a water-bath at 40° C. The residue is taken up in chloroform and introduced into the top of a column (L: 40 cm; $\phi$: 2 cm) containing Merck ®60 silica gel (70–230 mesh) in chloroform, elution is carried out in 200 ml of chloroform, 200 ml of a 1/99 mixture of methanol and chloroform, 200 ml of a 2/98 mixture of methanol and chloroform, 200 ml of a 3/97 mixture of methanol and chloroform, 200 ml of a 4/96 mixture of methanol and chloroform, 400 ml of a 5/95 mixture of methanol and chloroform, 400 ml of a 6/94 mixture of methanol and chloroform and 200 ml of a 10/90 mixture of methanol and chloroform and the eluate is fractionated. The fractions containing the product are evaporated, the residue is taken up in ether and triturated and the solid is filtered off and dried.

Yield: 350 mg (53%)

3. H—His—Sta—Ala—Sta—OMe.2TFA 220 mg of Boc—His—Sta—Ala—Sta—OMe are covered with 3 ml of TFA. After 30 minutes at AT, the solvent is evaporated off, the residue is taken up in ether and the solid is filtered off and dried immmediately over $P_2O_5$.

Yield: 235 mg (91%)

4. Boc—Trp—His—Sta—Ala—Sta—OMe (SR 41619)

235 mg of H—His—Sta—Ala—Sta—OMe.2TFA are covered with 30 ml of dioxane containing 68 mg of NEM. 170 mg of Boc—Trp—ONp and 54 mg of HOBt are added. The pH is adjusted to 6–7 with NEM and the mixture is stirred for 48 hours at AT. The solvent is evaporated off in vacuo, the residue is taken up in water, extraction is carried out with methylene chloride and the organic phase is washed with water and then with 5% strength $NaHCO_3$ solution and water. It is dried over $Na_2SO_4$. The solvent is evaporated off. The residue is dissolved in chloroform and introduced into the top of a column (L: 60 cm; $\phi$: 2 cm) containing Merck ®60 silica gel (60–230 mesh) in chloroform. Elution is carried out with 100 ml of chloroform, 100 ml of a 1/99 mixture of methanol and chloroform, 100 ml of a 2/98 mixture of methanol and chloroform, 100 ml of a 3/97 mixture of methanol and chloroform, 300 ml of a 4/96 mixture of methanol and chloroform, 500 ml of a 5/95 mixture of methanol and chloroform and 300 ml of a 10/90 mixture of methanol and chloroform. The eluate is fractionated. The fractions containing the product are evaporated, the residue is taken up in ether and the solid is filtered off and dried.

| Yield: | 75 mg (32%) |
|---|---|
| Aminoacid analysis: | Ala: 0.89 (1) |
| | His: 0.80 (1) |
| | Trp: 0.77 (1) |
| | Sta: 2.31 (2) |

NMR spectrum:

| δ | appearance | integration | assignment |
|---|---|---|---|
| 0.50–1.57 | m | 30 H | $^6C(CH_3)_2$ Sta, $CH_3$ Ala, $(CH_3)_3C$ Boc, $^5CH_2-^6CH$ Sta |
| 1.96–2.38 | m | 4 H | $^2CH_2$ Sta |
| 2.70–3.16 | m | 4 H | $^3CH_2$ Trp, His |
| 3.50 | s | 3 H | $CH_3$ ester |
| 3.67–3.88 | m | 4 H | $^4CH-^3CH$ Sta |
| 4.05–4.57 | m | 3 H | $^2CH$ Trp, His, Ala |
| 4.82–5.00 | m | 2 H | OH Sta |
| 6.72–7.59 | m | 10 H | aromatic protons Trp, His, 3 × NH |
| 7.95–8.20 | m | 2 H | 2 × NH |
| 10.74 | s | 1 H | NH indole |

EXAMPLE 28

Z—Tau—Phe—His—Sta—Ala—Sta—OCH₃ (SR 41748)

H—His—Sta—Ala—Sta—OCH₃.2TFA (360 mg; Example 27-3) is dissolved in 10 ml of DMF. The solution is brought to pH 7 by adding DIPEA. 195 mg of Z—Tau—Phe—OH and 221 mg of Bop are added successively thereto. The reaction mixture is brought to pH 7–8 by adding DIPEA and the mixture is stirred for 48 hours at AT and then evaporated to dryness. The product obtained is chromatographed on a column containing silica gel (diameter: 2 cm; height: 30 cm) and eluted with 300 ml of chloroform, 200 ml of a 98/2 mixture of chloroform and methanol, 200 ml of a 97/3 mixture of chloroform and methanol, 200 ml of a 96/4 mixture of chloroform and methanol, 200 ml of a 95/5 mixture of chloroform and methanol, 400 ml of a 94/6 mixture of chloroform and methanol and 400 ml of a 92/8 mixture of chloroform and methanol. The pure fractions (determined by TLC) are combined and evaporated to dryness under reduced pressure at AT. This gives an oil. This oil is purified again on a column containing silica gel (diameter: 2 cm; height: 25 cm) and eluted with 200 ml of a 99/1 mixture of chloroform and methanol, 200 ml of a 98.5/1.5 mixture of chloroform and methanol, 200 ml of a 98/2 mixture of chloroform and methanol, 200 ml of a 97.5/2.5 mixture of chloroform and methanol, 200 ml of a 97/3 mixture of chloroform and methanol, 100 ml of a 96/4 mixture of chloroform and methanol, 100 ml of a 94/6 mixture of chloroform and methanol, 100 ml of a 92/8 mixture of chloroform and methanol, 100 ml of a 90/10 mixture of chloroform and methanol, 100 ml of an 88/12 mixture of chloroform and methanol, 100 ml of an 86/14 mixture of chloroform and methanol and 100 ml of an 84/16 mixture of chloroform and methanol. The pure fractions (determined by TLC) are combined and evaporated to dryness. The residue is taken up in ethyl acetate (20 ml). The organic phase is washed with a saturated aqueous solution of sodium bicarbonate (10 ml) and an aqueous solution of sodium chloride (10 ml) and then dried over magnesium sulphate and evaporated to dryness. The residue is taken up in ether and triturated and the solid is filtered off. 60 mg of a cream powder are obtained.

TLC: 90/20/3 mixture of chloroform, methanol and acetic acid; Rf = 0.48.

| Aminoacid analysis: | Ala: 0.97 |
|---|---|
| | Sta: 1.99 |
| | Tau—Phe: 1.19 |
| | His: 0.86. |

NMR spectrum:

| δ | appearance | integration | assignment |
|---|---|---|---|
| 0.77 | m | 12 H | $^6C(CH_3)_2$ Sta, $^5CH_2-^6CH$ Sta |
| 0.87–1.56 | m | 9 H | $CH_3$ Ala |
| 1.91–2.4 | m | 4 H | $^2CH_2$ Sta |
| 2.5–3.45 | m | 8 H(*) | $^3CH_2$ Phe, His, $^2CH_2-^3CH_2$ Tau |
| 3.50 | s | 3 H | $CH_3$ Ester |
| 3.61–3.88 | m | 4 H | $^3CH-^4CH$ Sta |
| 4.05–4.55 | m | 3 H | $^2CH$ Phe, Ala, His |
| 4.95 | unresolved peaks | 4 H | $CH_2$ of Z, OH Sta |
| 6.77 | s | 1 H | $^4{'}CH$ His |
| 7.05–7.45 | m | 13 H | aromatic protons, 3 NH |
| 7.46 | s | 1 H | $^{2'}CH$ His |
| 7.66 | d | 1 H | NH |
| 7.96 | d | 1 H | NH |

| 8.14 | d | 1 H | NH |

(*)Integration perturbed by the presence of DOH

EXAMPLE 29 iVa—Phe—Phe—Sta—Ala—Sta—OMe (SR 41764)

130 mg of H—Phe—Sta—Ala—Sta—OMe (Example 1-6), 79.5 mg of iva—Phe—ONSu, 31 mg of HOBt and 75 mg of NEM are added successively to 3 ml of dioxane. The mixture is stirred at AT. The pH is adjusted to 6–7, if necessary, with NEM. After 24 hours, the solid is filtered off, washed with a small amount of dioxane and then with ether and dried.

| Yield: | 110 mg (73%). |
| Aminoacid analysis: | Ala: 1.03 (1) |
| | Phe: 1.93 (2) |
| | Sta: 2.04 (2) |

NMR spectrum:

| δ | appearance | integration | assignment | |
|---|---|---|---|---|
| 0.51–0.93 | m | 18 H | $^6C(CH_3)_2$ | |
| | | | | Sta |
| | | | $^3C(CH_3)_2$ | iVa |
| 1.09–1.88 | m | 12 H | $^5CH_2$—$^6CH$ | Sta |
| | | | $CH_3$ | Ala |
| | | | $^3CH$—$^2CH_2$ | iVa |
| 1.88–2.40 | m | 4 H | $^2CH_2$ | Sta |
| 2.50–3.09 | m | 4 H | $^2CH_2$ | Phe |
| 3.5 | s | 3 H | $CH_3$ | COOCH$_3$ |
| | | | $^4CH$—$^3CH$ | Sta |
| 3.66–4.59 | m | 7 H | $^2CH$ | Phe |
| | | | $^2CH$ | Ala |
| 4.8 | d | 1 H | OH | Sta |
| 4.95 | d | 1 H | OH | Sta |
| 7.01–7.27 | m | 10 H | aromatic protons | |
| 7.37 | d | 1 H | NH | |
| 7.46 | d | 1 H | NH | |
| 7.77 | d | 1 H | NH | |
| 7.88 | d | 1 H | NH | |

EXAMPLE 30 iVa—Phe—Leu—Sta—Ala—Sta—OMe (SR 41765)

1. Boc—Leu—Sta—Ala—Sta—OMe 354 mg of H—Sta—Ala—Sta—OMe.TFA (Example 1-3) are covered with 30 ml of dioxane containing 75 mg of NEM, and 260 mg of Boc—Leu—ONSu are then added. The mixture is stirred at AT. The pH is adjusted to 6–7, if necessary, with NEM. After 48 hours, the solvent is evaporated off under a waterpump vacuum in a water-bath at 47° C., the residue is taken up in iced water, extraction is carried out with methylene chloride and the organic phase is dried over Na$_2$SO$_4$. It is evaporated. The residue is dissolved in chloroform and introduced into the top of a column (L: 40 cm; diameter: 2 cm) containing Merck 60 silica gel (70–230 mesh) in chloroform. Elution is carried out with 200 ml of chloroform, 200 ml of a 1/99 mixture of methanol and chloroform, 200 ml of a 2/98 mixture of methanol and chloroform, 200 ml of a 3/97 mixture of methanol and chloroform and 200 ml of a 4/96 mixture of methanol and chloroform. The eluate is fractionated and the fractions containing the pure product are evaporated. The residue is taken up in ether. The solid is filtered off and dried.

Yield: 160 mg (38%)

2. H—Leu—Sta—Ala—Sta—OMe.TFA 140 mg of Boc—Leu—Sta—Ala—Sta—OMe are covered with 2 ml of TFA. After 30 minutes at AT, the solvent is evaporated off, the residue is taken up in ether and the solid obtained is filtered off and dried.

Yield: 140 mg (100%).

3. iVa—Phe—Leu—Sta—Ala—Sta—OMe 110 mg of H—Leu—Sta—Ala—Sta—OMe, 79.5 mg of iVa—Phe—ONSu and 31 mg of HOBt are covered with 3 ml of dioxane containing 75 mg of NEM. The mixture is stirred at AT and the pH is adjusted to 6–7, if necessary, with NEM. After 24 hours, the solid is filtered off, washed with dioxane and then with ether and dried.

| Yield: | 80 mg (55%). |
| Aminoacid analysis: | Ala: 1.02 (1) |
| | Leu: 1.01 (1) |
| | Phe: 0.9 (1) |
| | Sta: 2.00 (2) |

NMR spectrum:

| δ | appearance | integration | assignment | |
|---|---|---|---|---|
| 0.45–1.88 | m | 24 H | $^6C(CH_3)_2$ | Sta |
| | | | $^4C(CH_3)_2$ | Leu |
| | | | $^3C(CH_3)_2$ | iVa |
| | | 15 H | $^5CH_2$—$^6CH$ | Sta |
| | | | $CH_3$ | Ala |
| 1.03–1.88 | m | 15 H | $^3CH$—$^2CH_2$ | iVa |
| | | | $^4CH$—$^3CH_2$ | Leu |
| 1.95–2.4 | m | 4 H | $^2CH_2$ | Sta |
| 2.58–3.03 | m | 2 H | $^2CH_2$ | Phe |
| 3.5 | s | 3 H | $CH_3$ | COOCH$_3$ |
| | | | $^4CH$—$^3CH$ | Sta |
| | | | $^2CH$ | Phe |
| 3.64–4.61 | m | 7 H | $^2CH$ | Ala |
| | | | $^2CH$ | Leu |
| 7.04–7.24 | m | 5 H | aromatic protons | |
| 7.24–7.42 | m | 2 H | 2 NH | |
| 7.83 | d | 1 H | NH | |
| 7.90–8.09 | m | 2 H | 2 NH | |

EXAMPLE 31 iVa—Phe—Phe—Sta—Ala—isoSta—OMe (SR 41766)

The procedure of Example 29 is followed, the methyl ether of statine being replaced in the first step by its isostatine isomer. In the same way, the expected product is isolated in the form of a solid.

| Aminoacid analysis: | Ala: 1.00 (1) |
| | Phe: 2.00 (2) |
| | Sta: 2.01 (2) |

NMR spectrum:

| δ | appearance | integration | assignment | |
|---|---|---|---|---|
| 0.50–0.90 | m | 18 H | $^6C(CH_3)_2$ | isoSta |
| | | | $^6C(CH_3)_2$ | Sta |
| | | | $^3C(CH_3)_2$ | iVa |
| | | | $^5CH_2$—$^6CH$ | Sta |
| | | | $^5CH_2$—$^6CH$ | isoSta |
| 1.04–1.85 | m | 12 H | $CH_3$ | Ala |
| | | | $^3CH$—$^2CH_2$ | iVa |
| 1.91–2.5 | m | 4 H | $^2CH_2$ | Sta |
| | | | $^2CH_2$ | isoSta |
| 2.5–3.08 | m | 4 H | $^2CH_2$ | Phe |
| 3.51 | s | 3 H | $CH_3$ | COOCH$_3$ |
| | | | $^4CH$—$^3CH$ | Sta |
| | | | $^4CH_3$—$CH$ | isoSta |
| 3.54–4.62 | m | 7 H | $^2CH$ | Phe |
| | | | $^2CH$ | Ala |

-continued

| | | | | | |
|---|---|---|---|---|---|
| 4.80 | d | 1 H | ⎧ | OH | Sta |
| 4.91 | d | 1 H | ⎩ | OH | isoSta |
| 7.01–7.25 | m | 10 H | | aromatic protons | |
| 7.41 | d | 1 H | | NH | |
| 7.53 | d | 1 H | | NH | |
| 7.77 | d | 1 H | | NH | |
| 7.91 | d | 1 H | | NH | |
| 8.11 | d | 1 H | | NH | |

EXAMPLE 32

$C_6H_5CH_2CH_2CO$—Phe—Phe—Sta—Ala—Sta—OMe (SR 41768)

130 mg of H—Phe—Sta—Ala—Sta—OMe.TFA (Example 1-6), 91 mg of $C_6H_5$—$CH_2$—$CH_2$—CO—Phe—ONSu and 31 mg of HOBt are introduced successively into The mixture is stirred at AT. The pH is adjusted to 6–7, if necessary, with NEM. After 24 hours, the solid is filtered off, washed with dioxane and then with ether and dried.

Yield: 115 mg (71%).
Aminoacid analysis: Ala: 1.01 (1)
Phe: 1.99 (2)
Sta: 2.00 (2)

NMR spectrum:

| δ | appearance | integration | assignment | |
|---|---|---|---|---|
| 0.69–0.87 | m | 12 H | $^6C(CH_3)_2$ | Sta |
| 1.08–1.59 | m | 9 H | ⎰ $^5CH_2$—$^6CH$ | Sta |
| | | | ⎱ $CH_3$ | Ala |
| 1.88–2.40 | m | 8 H | $^2CH_2$ | Sta |
| | | | $^3CH_2$—$^2CH_2$ | $C_6H_5$ |
| | | | | $(CH_2)_2$ |
| 2.48–3.11 | m | 4 H | $CH_2$ | Phe |
| 3.5 | s | 3 H | $CH_3$ | $COOCH_3$ |
| 3.67–4.56 | m | 7 H | ⎰ $^4CH$—$^3CH$ | Sta |
| | | | $^2CH$ | Phe |
| | | | ⎱ $^2CH$ | Ala |
| 4.79 | d | 1 H | ⎧ OH | Sta |
| 4.93 | d | 1 H | ⎩ OH | Sta |
| 6.98–7.25 | m | 15 H | aromatic protons | |
| 7.35 | d | 1 H | NH | |
| 7.45 | d | 1 H | NH | |
| 7.77 | d | 1 H | NH | |
| 7.98 | d | 1 H | NH | |
| 8.14 | d | 1 H | NH | |

EXAMPLE 33 iVa—Phe—Nle—Sta—Ala—Sta—OMe (SR 41979)

1. Boc—Nle—Sta—Ala—Sta—OMe 31 mg of H—Sta—Ala—Sta—OMe.TFA (Example 1-4), 393 mg of Boc—Nle—ONSu and 162 mg of HOBt are covered with 5 ml of dioxane containing 391 mg of NEM. The pH is adjusted to 6–7, if necessary, with NEM and the mixture is stirred for 48 hours at AT. The solvent is evaporated off, the residue is dissolved in AcOEt and the solution is washed successively with 5% strength $KHSO_4$-$K_2SO_4$ solution, water/NaCl, 5% strength $NaHCO_3$ solution and water/NaCl. It is dried over $MgSO_4$ and the solvent is evaporated off. The residue is dissolved in ether and the product is precipitated with pentane, filtered off and dried.

Yield: 570 mg (90%)

2. Boc—Nle—Sta—Ala—Sta—OME.TFA 70 mg of Boc—Nle—Sta—Ala—Sta—OMe are covered with 5 ml of TFA. After 15 minutes at AT, the solvent is evporated off and the residue is taken up in a 1/1 mixture of ether and hexane. The solid is filtered off and dried in vacuo.

Yield: 570 mg (100%).

3. iVa—Phe—Nle—Sta—Ala—Sta—OMe (SR 41919)

150 mg of H—Nle—Sta—Ala—Sta—OMe.TFA, 36 mg of HOBt and 94 mg of iVa—Phe—ONSu are added to 3 ml of dioxane containing 89 mg of NEM. The mixture is stirred at AT. The pH is adjusted to 6–7, if necessary, with NEM. After 24 hours, the solid is filtered off, washed with dioxane and then with ether and dried.

Yield: 130 mg (73%).
Aminoacid analysis: Ala: 1.02 (1)
Nle: 1.01 (1)
Sta: 1.95 (2)
Phe: 1.01 (1)

NMR spectrum:

| δ | appearance | integration | assignment | |
|---|---|---|---|---|
| 10.59–0.91 | m | 21 H | ⎧ $^6C(CH_3)_2$ | Sta |
| | | | ⎨ $CH_3$ | Nle |
| | | | ⎩ $^3C(CH_3)_2$ | iVa |
| 1.09–1.95 | m | 18 H | ⎧ $^5CH_2$—$^6CH$ | Sta |
| | | | ⎪ $CH_3$ | Ala |
| | | | ⎨ $^3CH$—$^2CH_2$ | iVa |
| | | | ⎩ $CH_2$—$CH_2$—$CH_2$ | Nle |
| 1.95–2.38 | m | 4 H | $^2CH_2$ | Sta |
| 2.56–3.08 | m | 2 H | $^3CH_2$ | Phe |
| 3.53 | s | 3 H | $CH_3$ | $COOCH_3$ |
| 3.62–4.59 | m | 7 H | ⎧ $^4CH$—$^3CH$ | Sta |
| | | | ⎪ $^2CH$ | Phe |
| | | | ⎨ $^2CH$ | Ala |
| | | | ⎩ $^2CH$ | Nle |
| 4.83 | d | 1 H | ⎧ OH | Sta |
| | | | | Sta |
| 4.95 | d | 1 H | ⎩ OH | |
| 7.01–7.29 | m | 5 H | aromatic protons | |
| 7.37 | 2 d | 2 H | 2 NH | |
| 7.85 | d | 1 H | NH | |
| 8 | 2 d | 2 H | 2 NH | |

EXAMPLE 34

$C_6H_5SO_2$—Phe—Phe—Sta—Ala—Sta—$OCH_3$ (SR 41938)

300 mg of H—Phe—Sta—Ala—Sta—$OCH_3$.TFA (Example 1-6) are dissolved in 25 ml of DMF. The solution is brought to pH 7 by adding DIPEA. 146 mg of $C_6H_5$—$SO_2$—Phe—OH, 99 mg of DCCI and 74 mg of HOBt (product containing 13% of water) are added successively to this solution and the pH is then brought to 7 by adding DIPEA. The reaction mixture is stirred overnight at AT and then evaporated to dryness under reduced pressure. The residue is taken up in 20 ml of methylene chloride. The DCU formed is filtered off. The methylene chloride phase is washed successively with a saturated aqueous solution of sodium bicarbonate (2×10 ml), an aqueous solution of $KHSO_4$-$K_2SO_4$ (pH 2) (2×10 ml) and water (2×10 ml) and then dried over magnesium sulphate and evaporated to dryness under reduced pressure. The residue is taken up in a small amount of ether and the solid is filtered off; 300 mg of a white powder are obtained. The crude product is then purified by chromatography on a column containing silica gel (diameter: 2 cm; height: 25 cm) and eluted with 300 ml of chloroform, 100 ml of an 80/20 mixture of chloroform and methanol, 100 ml of a 60/40 mixture of chloroform and methanol and 100 ml of a 40/60 mixture of chloroform and methanol. The various fractions are determined by TLC. The following are collected: a fraction A (10 mg), which is discarded, and a fraction B. After the solvents have been evaporated off and the residue has been taken up in ether, 130 mg of a white powder are obtained (yield: 34.5%).

TLC: 90/20/3 mixture of chloroform, methanol and acetic acid; Rf: 0.71.
Elementary analysis:

| | | | |
|---|---|---|---|
| Calculated | C 62.02 | H 7.21 | N 8.22 |
| Found | C 62.07 | H 7.03 | N 8.17 |

NMR spectrum:

| δ | appearance | integration | assignment | |
|---|---|---|---|---|
| 0.76 | m | 12 H | $^6C(CH_3)_2$ | Sta |
| 0.92–1.59 | m | 9 H | $^5CH_2$—$^6CH$ | Sta |
| | | | $CH_3$ | Ala |
| 1.8–2.38 | m | 4 H | $^2CH_2$ | Sta |
| 2.5–3.05 | m | 4 H | $^3CH_2$ | Phe |
| 3.50 | s | 3 H | $CH_3$ | ester |
| 3.62–3.90 | m | 4 H | $^3CH$—$^4CH$ | Sta |
| 4.00 | m | 1 H | $^2CH$ Phe, Phe, Ala | |
| 4.21 | m | 2 H | | |
| 4.75 | d | 1 H | OH | Sta |
| 4.93 | d | 1 H | OH | Sta |
| 6.69–7.49 | m | 17 H | aromatic protons 2 NH | |
| 7.74 | d | 1 H | NH | |
| 7.93 | bs (broadened singlet) | 1 H | NH | |
| 8.19 | d | 1 H | NH | |

EXAMPLE 35

$C_6H_5CH_2SO_2$—Phe—Phe—Sta—Ala—Sta—$OCH_3$
(SR 41939)

The procedure of Example 34 is followed, the $C_6H_5$—$SO_2$-Phe—OH being replaced by an equivalent amount of $C_6H_5$—$CH_2SO_2$—Phe—OH.

The expected product is isolated in the same way.

NMR spectrum:

| δ | appearance | integration | assignment | |
|---|---|---|---|---|
| 0.74 | m | 12 H | $^6C(CH_3)_2$ | Sta |
| 0.93–1.53 | m | 9 H | $^5CH_2$—$^6CH$ | Sta |
| | | | $CH_3$ | Ala |
| 1.85–2.37 | m | 4 H | $^2CH_2$ | Sta |
| 2.54–3.13 | m | 4 H | $^3CH_2$ | Phe |
| 3.43–3.67 | m | 5 H | $CH_3$ ester $CH_2$ of $C_6H_5$—$CH_2$—$SO_2$— | |
| 3.67–3.88 | m | 4 H | $^3CH$—$^4CH$ | Sta |
| 4.04 | m | 1 H | $^2CH$ Phe, Phe, Ala | |
| 4.20 | m | 1 H | | |
| 4.61 | m | 1 H | | |
| 4.80 | d | 1 H | OH | Sta |
| 4.94 | d | 1 H | OH | Sta |
| 6.93–7.66 | m | 18 H | aromatic protons 3 NH | |
| 7.79 | d | 1 H | NH | |
| 8.37 | d | 1 H | NH | |

EXAMPLE 36

Ac—Phe—Nva—Sta—Ala—Sta—OMe (SR 41994)

1. Boc—Nva—Sta—Ala—Sta—OMe 531 mg of H—Sta—Ala—Sta—OMe.TFA (Example 1-4), 162 mg of HOBt and 378 mg of Boc—Nva—ONSu are added successively to 50 ml of AcOEt containing 391 mg of NEM. The mixture is stirred at AT and the pH is adjusted to 6–7, if necessary, with NEM. After 24 hours, the organic solution is washed successively with a 5% strength solution of $KHSO_4$-$K_2SO_4$, NaCl/water, a 5% strength solution of $NaHCO_3$ and NaCl/water. It is dried over $MgSO_4$ and the solvent is evaporated off. The residual oil is taken up in ether and the mixture is left to stand; a precipitate forms, which is filtered off, washed with a small amount of ether and dried.

Yield: 320 mg (51%)

2. H—Nva—Sta—Ala—Sta—OMe.TFA 300 mg of Boc—Nva—Sta—Ala—Sta—OMe are covered with 2 ml of TFA. After 20 minutes at AT, the solvent is evaporated off, the residue is taken up in ether and the solid is filtered off and dried.

Yield: 300 mg (100%).

3. Ac—Phe—Nva—Sta—Ala—Sta—OMe 100 mg of H—Nva—Sta—Ala—Sta—OME.TFA, 23 mg of HOBt and 53 mg of Ac—Phe—ONSu are added successively to 5 ml of AcOEt containing 58 mg of NEM. The mixture is stirred at AT and the pH is adjusted to 6–7, if necessary, with NEM. After 24 hours, the solid is filtered off, washed with AcOEt and then with ether and dried.

Yield: 70 mg (63%).
Aminoacid analysis: Ala: 1.00 (1)
Nva: 1.00 (1)
Sta: 2.00 (2)
Phe: 1.00 (1)

NMR spectrum:

| δ | appearance | integration | assignment | |
|---|---|---|---|---|
| 0.64–0.93 | m | 15 H | $^6C(CH_3)_2$ | Sta |
| | | | $CH_3$ | Nva |
| 1.08–1.83 | m | 16 H | $^5CH_2$—$^6CH$ | Sta |
| | | | $CH_3$ | Ala |
| | | | $CH_2$—$CH_2$ | Nva |
| | | | $CH_3$ | Ac |
| 1.96–2.41 | m | 4 H | $^2CH_2$ | Sta |
| 2.56–3.04 | m | 2 H | $^2CH_2$ | Phe |
| 3.5 | s | 3 H | $CH_3$ | $COOCH_3$ |
| 3.67–4.56 | m | 7 H | $^4CH$—$^3CH$ | Sta |
| | | | $^2CH$ | Phe |
| | | | $^2CH$ | Ala |
| | | | $^2CH$ | Nva |
| 4.83 | d | 1 H | OH | Sta |
| 4.96 | d | 1 H | OH | Sta |
| 7.08–7.32 | m | 5 H | aromatic protons | |
| 7.32–7.50 | m | 2 H | 2 NH | |
| 7.95 | d | 1 H | NH | |
| 8.08–8.25 | m | 2 H | 2 NH | |

EXAMPLE 37 iVa—Phe—Nva—Sta—Ala—Sta—OMe (SR 41995)

The procedure of Example 36-3 is followed, the Ac—Phe—ONSu being replaced by an equivalent amount of iva—Phe—ONSu. The expected product is obtained in the same way.

| Aminoacid analysis: | Ala: 1.02 (1) |
|---|---|
| | Nva: 1.00 (1) |
| | Sta: 1.96 (2) |
| | Phe: 1.02 (1) |

NMR spectrum:

| δ | appearance | integration | assignment | |
|---|---|---|---|---|
| 0.54–0.91 | m | 21 H | $^6C(CH_3)_2$ | Sta |
| | | | $^3C(CH_3)_2$ | iVA |
| | | | $CH_3$ | Nva |
| 1.08–1.88 | m | 16 H | $^5CH_2$—$^6CH$ | Sta |
| | | | $CH_3$ | Ala |
| | | | $^3CH$—$^2CH_2$ | iVa |
| | | | $CH_2$—$CH_2$ | Nva |
| 1.96–2.37 | m | 4 H | $^2CH_2$ | Sta |
| 2.56–3.03 | m | 2 H | $^2CH_2$ | Phe |
| 3.5 | s | 3 H | $CH_3$ | COOCH$_3$ |
| 3.67–4.59 | m | 7 H | $^4CH$—$^3CH$ | Sta |
| | | | $^2CH$ | Phe |
| | | | $^2CH$ | Ala |
| | | | $^2CH$ | Nva |
| 4.82 | d | 1 H | OH | Sta |
| 4.95 | d | 1 H | OH | Sta |
| 7.03 | m | 5 H | aromatic protons | |
| 7.35 | 2 d | 2 H | 2 NH | |
| 7.85 | d | 1 H | NH | |
| 7.93–8.08 | m | 2 H | 2 NH | |

EXAMPLE 38

Boc—Phe—Nva—Sta—Ala—Sta—OMe (SR 41996)

This produtt is obtained as in Example 36-3, the Ac—Phe—ONSu being replaced by an equivalent amount of Boc—Phe—ONSu.

| Aminoacid analysis: | Ala: 0.99 (1) |
|---|---|
| | Nva: 1.00 (1) |
| | Sta: 2.01 (2) |
| | Phe: 1.01 (1) |

NMR spectrum:

| δ | appearance | integration | assignment | |
|---|---|---|---|---|
| 0.69–0.90 | m | 15 H | $^6C(CH_3)_2$ | Sta |
| | | | $CH_3$ | Nva |
| 1.06–1.69 | m | 22 H | $^5CH_2$—$^6CH$ | Sta |
| | | | $CH_3$ | Ala |
| | | | $C(CH_3)_3$ | Boc |
| | | | $CH_2$—$CH_2$ | Nva |
| 1.95–2.40 | m | 4 H | $^2CH_2$ | Sta |
| 2.53–3.00 | m | 2 H | $^2CH_2$ | Phe |
| 3.51 | s | 3 H | $CH_3$ | COOCH$_3$ |
| 3.64–4.32 | m | 7 H | $^4CH$—$^3CH$ | Sta |
| | | | $^2CH$ | Nva |
| | | | $^2CH$ | Ala |
| | | | $^2CH$ | Phe |
| 4.81 | d | 1 H | OH | Sta |
| 4.95 | d | 1 H | OH | Sta |
| 6.95 | d | 1 H | NH | |
| 7.06–7.30 | m | 5 H | aromatic protons | |
| 7.35 | d | 1 H | | NH |
| 7.45 | d | 1 H | NH | |
| 7.90 | 2 d | 2 H | 2 NH | |

EXAMPLE 39

Boc—Ile—His—Sta—Ala—Sta—OMe (SR 42019)

1. Boc—Ile—His—Sta—OMe 710 mg of Boc—His(Boc)—Sta—OMe (Example 8-1) are covered with 8 ml of TFA. After 15 minutes at AT, the solvent is evaporated off, the residue is taken up in ether and the latter is evaporated off. The residual oil is solubilised in 10 ml of DMF, DIPEA is added until a pH of 6–7 is obtained, and a solution of 475 mg of Boc—Ile—OH in 10 ml of DMF containing 258 mg of DIPEA is then added, followed by a solution of 986 mg of Bop in 10 ml of DMF containing 287 mg of DIPEA. The mixture is stirred at AT and the pH is adjusted to 6–7, if necessary, with DIPEA. After 24 hours, the DMF is evaporated off under a high vacuum in a water-bath at 40° C., the residue is taken up in AcOEt and the solution is washed with a 5% strength solution of NaHCO$_3$ and NaCl/water. It is dried over MgSO$_4$ and evaporated. The product is dissolved in a 5/95 mixture of MeOH and chloroform and introduced into the top of a column containing Merck 60 silica gel (70–230 mesh) (L: 40 cm; diameter: 3 cm). Elution is carried out with mixtures of MeOH and chloroform with a gradient up to 20/50. The fractions containing the pure product are evaporated. The residue is taken up in water; the solid is filtered off and dried.

Yield: 430 mg (43%).

TLC: 80/15/5 mixture of chloroform, MeOH and acetic acid.

2. Boc—Ile—His—Sta—OH 10 mg of Boc—Ile—His—Sta—OMe are solubilised in 25 ml of DMF. 2 ml of distilled water are added and 1.5 ml of normal sodium hydroxide solution are then added at AT. The mixture is stirred for 30 minutes at AT and 1.5 ml of normal hydrochloric acid are then added. The solvents are evaporated off, the residue is taken up in the minimum amount of water and the solid is filtered off and dried. It is washed with ether and dried.

Yield: 320 mg (81%).

3. Boc—Ile—His—Sta—Ala—Sta—OMe 80 mg of Boc—Ala—Sta—OMe are covered with 3 ml of TFA. After 30 minutes at AT, the solvent is evaporated off to dryness. The residue is dissolved in 30 ml of dioxane and the solution is brought to pH 7–8 with DIPEA. 262 mg of Boc—Ile—His—Sta—OH and then 268 mg of Bop are added. The pH is adjusted to 6–7 with DIPEA. The mixture is stirred at AT and the pH is monitored several times. After 24 hours, the mixture is filtered and the solvent is evaporated off. The residue is dissolved in chloroform and introduced into the top of a column (L: 40 cm; diameter: 2 cm) containing Merck 60 silica gel (70–230 mesh) in chloroform. Elution is carried out with 00 ml of chloroform, 00 ml of a 1/99 mixture of MeOH and chloroform, 200 ml of a 2/98 mixture of MeOH and chloroform, 400 ml of a 4/96 mixture of MeOH and chloroform, 300 ml of a 6/94 mixture of MeOH and chloroform and 200 ml of a 10/90 mixture of MeOH and chloroform. The eluate is fractionated. The fractions containing the pure product are evaporated. The residue is taken up in a small amount of methylene chloride and the solid is filtered off, rinsed with ether and dried.

Yield: 80 mg (24%).

| Aminoacid analysis: | Ala: 1.02 (1) |
|---|---|
| | Ile: 0.97 (1) |
| | Sta: 1.98 (2) |
| | His: 1.00 (1) |

NMR spectrum:

| δ | appearance | integration | assignment | |
|---|---|---|---|---|
| 0.64–0.88 | m | 18 H | $^6C(CH_3)_2$ | Sta |

-continued

| δ | appearance | integration | assignment | |
|---|---|---|---|---|
| 0.91–1.70 | m | 21 H | 2CH₃ | Ile |
| | | | CH₃ | Ala |
| | | | ⁵CH₂—⁶CH | Sta |
| | | | ⁴CH₂—³CH | Ile |
| | | | Boc | |
| 1.88–2.41 | m | 4 H | ²CH₂ | Sta |
| 2.66–2.95 | m | 2 H | ³CH₂ | His |
| 3.50 | s | 3 H | CH₃ | ester |
| 3.61–3.91 | m | 5 H | ⁴CH—³CH | Sta |
| | | | ²CH | Ile |
| 4.09–4.25 | m | 1 H | ²CH | Ala |
| 4.38–4.56 | m | 1 H | ²CH | His |
| 4.74–5.12 | m | 2 H | OH | Sta |
| | | | OH | |
| 6.74–6.87 | (d + s) | 2 H | ⁴'CH | His |
| | | | NH | |
| 7.24–7.5 | 2 d | 2 H | 2 NH | |
| 7.67 | s | 1 H | ²'CH | His |
| 7.87–8.06 | 2 d | 2 H | 2 NH | |

EXAMPLE 40

CH₃(CH₂)₆—Co—Phe—Phe—Sta—Ala—Sta—OH (SR 42 62)

1. CH₃(CH₂)₆—Co—Phe—Phe—Sta—Ala—Sta—OMe

This product is prepared as indicated in Example 29, the iVa—Phe—ONSu being replaced by CH₃(CH₂)₆—CO—Phe—ONSu.

2. CH₃(CH₂)₆—CO—Phe—Phe—Sta—Ala—Sta—OH 150 mg of CH₃(CH₂)₆—CO—Phe—Phe—Sta—Ala—Sta—OMe are solubilised in 10 ml of DMSO to which 2 ml of distilled water and 2 ml of methanol are added, followed, at AT, by 1 ml of normal sodium hydroxide solution. The mixture is stirred for 4 hours at AT and 1 ml of normal hydrochloric acid is then added; the pH is then 5. The solvents are evaporated off under a high vacuum in a water-bath at 40° and the remaining DMSO is taken up in water. The solid is filtered off, washed with water and dried. It is washed with ether.

Yield: 130 mg (88%).
Aminoacid analysis: Ala: 0.99 (1)
Sta: 1.94 (2)
Phe: 2.03 (2)

NMR spectrum:

| δ | appearance | integration | assignment | |
|---|---|---|---|---|
| 0.69–0.87 | m | 15 H | ⁶C(CH₃)₂ | Sta |
| | | | CH₃ | octyl |
| 0.87–1.61 | m | 21 H | ⁵CH₂—⁶CH | Sta |
| | | | CH₃ | Ala |
| | | | —(CH₂)₆ | octyl |
| 1.74–2.29 | m | 4 H | ²CH₂ | Sta |
| 2.51–3.06 | m | 4 H | ³CH₂ | Phe |
| 3.64–4.56 | m | 7 H | ⁴CH—³CH | Sta |
| | | | ²CH | Phe |
| | | | ²CH | Ala |
| 7.03–7.24 | m | 10 H | aromatic protons | |
| 7.33 | d | 1 H | NH | |
| 7.43 | d | 1 H | NH | |
| 7.75 | d | 1 H | NH | |
| 7.87 | d | 1 H | NH | |
| 8.06 | d | 1 H | NH | |

EXAMPLE 41 iVa—Phe—Nle—Sta—Ala—Sta—OH (SR 42128)

100 mg of iVa—Phe—Nle—Sta—Ala—Sta—OMe (Example 33-3) are solubilised in 10 ml of DMF at AT. 1 ml of distilled water is added and 0.26 ml of normal sodium hydroxide solution (2 equivalents) is then added at AT. The mixture is stirred for 30 minutes at AT, 0.26 ml of normal hydrochloric acid is then added and the pH is then 5. The solvents are evaporated off and the residue is taken up in water; the solid is filtered off, washed with water and then with ether and dried.

Yield: 75 mg.
Aminoacid analysis: Ala: 0.99 (1)
Nle: 1.00 (1)
Sta: 2.04 (2)
Phe: 0.98 (1)

NMR spectrum:

| δ | appearance | integration | assignment | |
|---|---|---|---|---|
| 0.58–0.91 | m | 21 H | ⁶C(CH₃)₂ | Sta |
| | | | CH₃ | Nle |
| | | | ³C(CH₃)₂ | iVa |
| 1.04–1.93 | m | 18 H | ⁵CH₂—⁶CH | Sta |
| | | | CH₃ | Ala |
| | | | ²CH₂—³CH | iVa |
| | | | —CH₂—CH₂—CH₂ | Nle |
| 1.93–2.29 | m | 4 H | ²CH₂ | Sta |
| 2.56–3.04 | m | 2 H | ³CH₂ | Phe |
| 3.64–4.61 | m | 7 H | ⁴CH—³CH | Sta |
| | | | ²CH | Phe |
| | | | ²CH | Ala |
| | | | ²CH | Nle |
| 7.06–7.29 | m | 5 H | aromatic protons | |
| 7.29–7.45 | m | 2 H | 2 NH | |
| 7.83 | d | 1 H | NH | |
| 8 | 2 d | 2 H | NH | |

EXAMPLE 42

Arginine salt of Boc—phe—Phe—Sta—Ala—Sta—OH

1. Boc—Phe—Phe—Sta—Ala—Sta—OH 270 mg of Boc—Phe—Phe—Sta—Ala—Sta—OMe (Example 4) are solubilised in 10 ml of DMF at AT. 1 ml of distilled water and then 0.66 ml of normal sodium hydroxide solution are added. The mixture is stirred for 30 minutes at AT and 0.66 ml of normal hydrochloric acid is then added; the pH is then 6 to pH paper. The solvents are evaporated off under a high vacuum. The residue is taken up in water and triturated and the solid is filtered off, washed with water and then with ether and dried.

Yield: 230 mg (87%).
Aminoacid analysis: Ala: 0.96 (1)
Sta: 2.00 (2)
Phe: 2.04 (2)

NMR spectrum:

| δ | appearance | integration | assignment | |
|---|---|---|---|---|
| 0.65–0.95 | m | 12 H | ⁶C(CH₃)₂ | Sta |
| 0.95–1.68 | m | 18 H | ⁵CH₂—⁶CH | Sta |
| | | | CH₃ | Ala |
| | | | Boc | Phe |
| 1.93–2.45 | m | 4 H | ²CH₂ | Sta |
| 2.54–3.14 | m | 4 H | ³CH₂ | Phe |
| 3.66–3.90 | m | 4 H | ⁴CH—³CH | Sta |
| 3.90–4.30 | m | 2 H | ²CH | Phe |
| 4.46–4.66 | m | 1 H | ²CH | Ala |
| 6.85 | d | 1 H | NH | |
| 7.04–7.27 | m | 10 H | aromatic protons | |

| | | | |
|---|---|---|---|
| 7.36 | d | 1 H | NH |
| 7.57 | d | 1 H | NH |
| 7.80 | d | 1 H | NH |
| 7.96 | d | 1 H | NH |

2. Arginine salt 4.8 mg of anhydrous H—Arg—OH are solubilised in 3 ml of distilled water, and a solution of 159.4 mg of Boc—Phe—Phe—Sta—Ala—Sta—OH in 10 ml of methanol is added to this solution. The mixture is stirred at AT for 15 minutes and evaporated to dryness. The residue is taken up in ether and the solid is filtered off and dried in vacuo.

Yield: 170 mg (89%).

EXAMPLE 43 iVa—Phe—Lys(Z)—Sta—Ala—Sta—OMe (SR 42130)

1. Boc—Lys(Z)—Sta—OEt 951 mg of H—Sta—OEt.TFA, 486 mg of HOBt and 1.71 g of Boc—Lys(Z)—ONSu are added successively to 50 ml of ethyl acetate containing 1.17 g of NEM. The mixture is stirred at AT and the pH is adjusted to 6-7, if necessary, with NEM. After 24 hours, the organic solution is washed successively with KHSO4-K2SO4 solution, water/NaCl, 5% strength NaHCO3 solution and water/NaCl. It is dried over MgSO4, the solvent is evaporated off to dryness and the residue is triturated in ether. The solid is filtered off and dried.

Yield: 1.17 g (75%); M.p.: 90°-93° C.

2. H—Lys(Z)—Sta—OEt.TFA (MB IV 563)

00 mg of Boc—Lys(Z)—Sta—OEt are covered with 8 ml of TFA at AT. After 15 minutes, the solvent is evaporated off, the residue is taken up in ether and the ether is evaporated off to give an oil, which is used as such.

3. iVa—Phe—Lys(Z)—Sta—OEt

The oil obtained, of H—Lys(Z)—Sta—OEt.TFA, is solubilised in 50 ml of AcOEt. 243 mg of HOBt are added and NEM is then added until a pH of 7-8 to pH paper is obtained. 623 mg of iVa—Phe—ONSu are added and the mixture is stirred at AT. The pH is adjusted to 6-7, if necessary, with NEM. After 24 hours, the solid is filtered off, washed with AcOEt and ether and dried.

Yield: 910 mg (87%).

4. iVa—Phe—Lys(Z)—Sta—OH 69 mg of iVa—Phe—Lys(Z)—Sta—OEt are solubilised in 30 ml of DMF. 3 ml of normal sodium hydroxide solution are added. The mixture is stirred for 30 minutes at AT and 3 ml of normal hydrochloric acid are then added; the pH is then 6-7 to pH paper. The solvents are evaporated off under a high vacuum in a water-bath at 40° C. The residue is triturated in water and the solid is filtered off, washed with water and then with ether and dried.

Yield: 800 mg (100%).

5. iVa—Phe—Lys(Z)—Sta—Ala—Sta—OMe 32 mg of Boc—Ala—Sta—OMe are covered with 5 ml of TFA at AT. After 15 minutes, the solvent is evaporated off to dryness; the residue is taken up in DMF (85 ml), the pH is brought to 7-8 with DIPEA, and a solution of 800 mg of iVa—Phe—Lys(Z)—Sta—OH in 0 ml of DMF containing 155 mg of DIPEA is then added, followed by a solution of 45 mg.

The mixture is stirred at AT for 24 hours. The DMF containing 186 mg of DIPEA is evaporated off. The residue is stirred at AT for 24 hours. The DMF is evaporated off under a high vacuum in a water-bath at 40°. The residue is taken up in water and the solid is filtered off, washed with water, ether, AcOEt and then ether and then dried.

Yield: 950 mg (87%).

| NMR spectrum: δ | appearance | integration | assignment | |
|---|---|---|---|---|
| 0.48–0.93 | m | 18 H | $^6$C(CH3)2 | Sta |
| | | | $^3$C(CH3)2 | iVa |
| 0.93–1.90 | m | 18 H | CH3 | Ala |
| | | | $^5$CH2—$^6$CH | Sta |
| | | | $^3$CH—$^2$CH2 | iVa |
| | | | β,γ,σ(CH2)3 | Lys |
| 1.96–2.37 | m | 4 H | $^2$CH2 | Sta |
| 2.58–3.04 | m | 4 H | εCH2 | Lys |
| | | | $^3$CH2 | Phe |
| 3.50 | s | 3 H | CH3 | COOCH3 |
| 3.64–3.88 | m | 4 H | $^4$CH—$^3$CH | Sta |
| 4.08–4.29 | m | 2 H | $^2$CH | Ala |
| | | | $^2$CH | Lys |
| 4.37–4.64 | m | 1 H | $^2$CH | Phe |
| 4.72–5.04 | 2d + 1s | 4 H | OH | |
| | | | OH | Sta |
| | | | CH2 | Z |
| 7.03–7.45 | m | 13 H | 2 aromatic protons | |
| | | | 3 NH | |
| 7.74–8.09 | 3 d | 3 H | 3 NH | |

EXAMPLE 44 iVa—Phe—Phe—Sta—Ala—Sta—NH2 (SR 42298)

1. H—Sta—OEt.TFA g of Boc—Sta—OEt are covered with 40 ml of TFA. The whole warms up slightly. After 20 minutes, the solvent is evaporated off to dryness, the residual oil is taken up in ether and the solid obtained is filtered off, washed with ether and dried.

Yield: 3.6 g (72%).

2. Boc—Phe—Sta—OEt 1.26 g of H—Sta—OEt.TFA, 648 mg of HOBt and 1.73 g of Boc—Phe—ONSu are added successively to 50 ml of ethyl acetate containing 1.56 g of NEM. The mixture is stirred at AT and the pH is adjusted to 6-7, if necessary, with NEM. After one night, the organic solution is washed successively with a 5% strength solution of KHSO4-K2SO4, H2O/NaCl, a 5% strength solution of NaHCO3 and H2O/NaCl. It is dried over MgSO4. The solvent is concentrated to a few ml and the solid obtained is filtered off, washed with ether and dried.

Yield: 1.39 g (77%).

3. H—Phe—Sta—OEt.TFA g of Boc—Phe—Sta—OEt are covered with 8 ml of TFA. After 20 minutes at AT, the solvent is evaporated off and ether and then pentane are added. The mixture is triturated in order to crystallise the oil, and the solid is filtered off, washed with pentane and dried in vacuo.

Yield: 1.01 g (100%).

4. iVa—Phe—Phe—Sta—OEt 1 g of H—Phe—Sta—OEt.TFA, 446 mg of HOBt and 1.15 g of iVa—Phe—ONSu are added successively to 20 ml of dioxane containing 1.08 g of NEM. The mixture is stirred at AT; the pH is adjusted to 6-7, if necessary, with NEM. After one night, the solid is filtered off, washed with dioxane and ether and dried.

Yield: 1.06 g (65%).

5. iVa—Phe—Phe—Sta—OH g of iVa—Phe—Phe—Sta—OEt are solubilised in 300 ml of DMF. 20 ml of distilled water are added and 4 ml of normal sodium hydroxide solution are then added at AT. The mixture is stirred for 30 minutes at AT and 4 ml of normal hydrochloric acid are then added; the pH is then 5. The solvents are evaporated off under a high vacuum in a water-bath at 40° C. The residue is taken up in water and the solid is filtered off, rinsed with ether and dried in vacuo.

Yield: 890 mg (93%).

6. Boc—Ala—Sta—NH$_2$ (MB IV 582)

500 mg of Boc—Ala—Sta—OMe are solubilised in 20 ml of methanol. The solution is cooled and 20 ml of liquid ammonia are added. The bomb is closed and left to stand for 4 days at AT. The bomb is cooled and, after it has been opened, nitrogen is bubbled in to drive off the ammonia, and the solvent is then evaporated off. The residue is taken up in a small amount of ether to give a white solid, which is filtered off and dried.

Yield: 300 mg (65%); M.p.: 175°–178° C.

7. H—Ala—Sta—NH$_2$.TFA 300 mg of Boc—Ala—Sta—NH$_2$ are covered with 3 ml of TFA at AT. After 20 minutes, the solvent is evaporated off, the residue is taken up in ether and triturated and the white solid is filtered off, washed with ether and dried.

Yield: 320 mg (103%).

8. iVa—Phe—Phe—Sta—Ala—Sta—NH$_2$ 107 mg of H—Ala—Sta—NH$_2$.TFA, 105 mg of iVa—Phe—Phe—Sta—OH and 162 mg of Bop are added successively to 10 ml of dioxane containing 124 mg of DIPEA. The mixture is stirred vigorously at AT; the pH is adjusted to 6–7, if necessary, with DIPEA. After one night, the precipitate is filtered off, washed with ethyl acetate and ether and dried.

Yield: 130 mg (58%).
Aminoacid analysis: Ala: 0.95 (1)
Sta: 2.04 (2)
Phe: 2.01 (2)

NMR spectrum:

| δ | appearance | integration | assignment | |
|---|---|---|---|---|
| 0.45–0.88 | m | 18 H | $^6$C(CH$_3$)$_2$ | Sta |
| | | | $^3$C(CH$_3$)$_2$ | iVa |
| | | | $^5$CH$_2$—$^6$CH | Sta |
| 1.06–2.12 | m | 16 H | CH$_3$ | Ala |
| | | | $^2$CH$_2$—$^3$CH | iVa |
| | | | $^2$CH$_2$ | Sta |
| 2.51–3.06 | m | 4 H | $^2$CH$_2$ | Phe |
| 3.61–4.59 | m | 7 H | $^4$CH—$^3$CH | Sta |
| | | | $^2$CH | Phe |
| | | | $^2$CH | Ala |
| 4.79–4.88 | m | 2 H | OH | Sta |
| | | | OH | |
| 6.75 | s | 1 H | NH | NH$_2$ |
| 7.00–7.27 | m | 11 H | 2 aromatic protons | Phe |
| | | | NH | NH$_2$ |
| 7.35 | d | 1 H | NH | |
| 7.5 | d | 1 H | NH | |
| 7.8 | d | 1 H | NH | |
| 7.88 | d | 1 H | NH | |
| 8.08 | d | 1 H | NH | |

EXAMPLE 45 t—BuAc—Phe—Phe—Sta—Ala—Sta—OMe (SR 42256)

114 mg of NEM, 200 mg of H—Phe—Sta—Ala—Sta—OMe.TFA (Example 1-6), 126 mg of t—BuAc—Phe—ONSu and 47 mg of HOBt are added successively to 10 ml of dioxane. The mixture is stirred at AT; the pH is adjusted to 6–7, if necessary, with NEM. After 24 hours, the dioxane is evaporated off, the residue is taken up in AcOEt and the solid is filtered off, washed with AcOEt and then with ether and dried.

Yield: 170 mg (72%).

NMR spectrum:

| δ | appearance | integration | assignment | |
|---|---|---|---|---|
| 0.66–0.95 | m | 21 H | $^6$C(CH$_3$)$_2$ | Sta |
| | | | $^3$C(CH$_3$)$_3$ | t-BuAc |
| | | | $^5$CH$_2$—$^6$CH | Sta |
| 1.08–1.61 | m | 9 H | | |
| | | | CH$_3$ | Ala |
| 1.82 | s | 2 H | $^2$CH$_2$ | t-BuAc |
| 1.88–2.40 | m | 4 H | $^2$CH$_2$ | Sta |
| 2.48–3.24 | m | 4 H | $^3$CH$_2$ | Phe |
| 3.51 | s | 3 H | CH$_3$ | COOCH$_3$ |
| | | | $^4$CH—$^3$CH | Sta |
| 3.69–4.59 | m | 7 H | $^2$CH | Phe |
| | | | $^2$CH | Ala |
| 4.8 | d | 1 H | OH | Sta |
| 4.96 | d | 1 H | OH | |
| 7.03–7.24 | m | 10 H | 2 aromatic protons | |
| 7.39 | d | 1 H | NH | |
| 7.46 | d | 1 H | NH | |
| 7.72–7.88 | m | 2 H | 2 NH | |
| 8.08 | d | 1 H | NH | |

EXAMPLE 46 iVa—Phe—Ala—Sta—Ala—Sta—OMe (SR 42258)

1. iVa—Phe—Ala—Sta—OMe 700 mg of Boc—Ala—Sta—OMe are covered with 5 ml of TFA. After 15 minutes at AT, the solvent is evaporated off to dryness and the residual oil is dissolved in 20 ml of dioxane; the pH is brought to 8 to pH paper with NEM, and 297 mg of HOBt and 761 mg of iVa—Phe—ONSu are then added. The mixture is stirred at AT; the pH is adjusted to 6–7, if necessary, with NEM. After 24 hours, the precipitate is filtered off, washed with AcOEt and ether and dried.

Yield: 750 mg (76%).

2. iVa—Phe—Ala—Sta—OH 91 mg of iVa—Phe—Ala—Sta—OMe are solubilised in 0 ml of DMF at AT. 2 ml of normal sodium hydroxide solution are added, the mixture is stirred for 40 minutes at AT and 2 ml of normal hydrochloric acid are then added; the pH is 5–6 to pH paper. The solvents are evaporated off under a high vacuum, the residue is taken up in water and the solid is filtered off and washed with water. It is dissolved in MeOH and the solution is evaporated to dryness. The residue is taken up again in the minimum amount of MeOH and the product is precipitated by adding ether. It is filtered off and dried.

Yield: 380 mg (79%).

3. iVa—Phe—Ala—Sta—Ala—Sta—OMe 80 mg of Boc—Ala—Sta—OMe are covered with 2 ml of TFA at AT. After 15 minutes at AT, the solvent is evaporated off and the residue is dissolved in 10 ml of dioxane; the pH is brought to 8 with DIPEA, and 238 mg of iVa—Phe—Ala—Sta—OH and 269 mg of Bop are added. The mixture is stirred at AT; the pH is adjusted to 6–7, if necessary, with DIPEA. After 24 hours the solid is filtered off, washed with AcOEt and ether and dried.

Yield: 320 mg (88%).

NMR spectrum:

| δ | appearance | integration | assignment | |
|---|---|---|---|---|
| 0.56–0.88 | m | 18 H | $^6C(CH_3)_2$ | Sta |
| | | | $^3C(CH_3)_2$ | iVa |
| 1.08–1.91 | m | 15 H(*) | $^2CH_3$ | Ala |
| | | | $^5CH_2$—$^6CH$ | Sta |
| | | | $^2CH_2$—$^3CH$ | iVa |
| 1.95–2.38 | m | 4 H | $^2CH_2$ | Sta |
| 2.59–3.17 | m | 2 H | $^2CH_2$ | Phe |
| 3.51 | s | 3 H | $CH_3$ | $COOCH_3$ |
| 3.66–3.90 | m | 4 H | $^4CH$—$^3CH$ | Sta |
| 4.06–4.35 | m | 2 H | $^2CH$ | Ala |
| 4.40–4.56 | m | 1 H | $^2CH$ | Phe |
| 4.82 | d | 1 H | OH | Sta |
| 4.95 | d | 1 H | OH | |
| 7.04–7.25 | m | 5 H | aromatic protons | |
| 7.29–7.41 | m | 2 H | 2 NH | |
| 7.90 | d | 1 H | NH | |
| 8.00 | d | 1 H | NH | |
| 8.08 | d | 1 H | NH | |

(*): Excess integration

EXAMPLE 47 iVa—Phe—Gly—Sta—Ala—Sta—OMe (SR 42261)

1. iVa—Phe—Gly—Sta—OMe 80 mg of Boc—Gly—Sta—OMe are covered with 3 ml of TFA at AT. After 15 minutes, the solvent is evaporated off to dryness. The residue is taken up in 10 ml of dioxane and the pH is brought to 8 with NEM. 118 mg of HOBt and 304 mg of iVa—Phe—ONSu are added. The mixture is stirred at AT and the pH is adjusted to 6–7, if necessary, with NEM. After 24 hours, the dioxane is evaporated off, the residue is dissolved in AcOEt and the solution is washed successively with a 5% strength solution of $KHSO_4$-$K_2SO_4$, water/NaCl, a 5% strength solution of $NaHCO_3$ and water/NaCl. It is dried over $MgSO_4$. The solvent is evaporated off, the residue is scratched in pentane and the solid is filtered off and dried.

Yield: 270 mg (70%).

2. iVa—Phe—Gly—Sta—OH 38 mg of iVa—Phe—Gly—Sta—OMe are solubilised in 10 ml of dioxane and 2 ml of MeOH at AT. 1 ml of normal sodium hydroxide solution is added and the mixture is stirred at AT for 1 hour. 1 ml of hydrochloric acid is added. The solvents are evaporated off to dryness, the residue is taken up in a small amount of water and triturated, the water is decanted, the residue is taken up in MeOH and the mixture is evaporated to dryness. The residue is triturated in ether and the solid is filtered off and dried.

Yield: 190 mg (82%).

3. iVa—Phe—Gly—Sta—Ala—Sta—OMe 44 mg of Boc—Ala—Sta—OMe are covered with 2 ml of TFA at AT. After 15 minutes, the solvent is evaporated off to dryness, the residue is dissolved in 10 ml of dioxane, the pH is brought to 7–8 with DIPEA, and 185 mg of iVa—Phe—Gly—Sta—OH and 215 mg of Bop are then added. The mixture is stirred at AT and the pH is adjusted to 6–7, if necessary, with DIPEA. After 24 hours, the mixture is filtered, the solvent is evaporated off, the residue is dissolved in AcOEt and the organic solution is washed successively with a 5% strength solution of $KHSO_4$-$K_2SO_4$, water/NaCl, a 5% strength solution of $NaHCO_3$ and water/NaCl. It is dried over $MgSO_4$ and the solvent is evaporated off. The product is dissolved in chloroform and introduced into the top of a column (L: 45 cm; diameter: 1.5 cm) containing Merck 60 silica gel (70–230 mesh) in chloroform. Elution is carried out with mixtures of MeOH and chloroform with a gradient from 1/99 to 5/95. The eluate is fractionated. The fractions containing the pure product are evaporated. The residue is taken up in pentane and the solid is filtered off and dried.

Yield: 120 mg (42%).

NMR spectrum:

| δ | appearance | integration | assignment | |
|---|---|---|---|---|
| 0.51–0.87 | m | 18 H | $^6C(CH_3)_2$ | Sta |
| | | | $^3C(CH_3)_2$ | iVa |
| 1.04–1.88 | m | 12 H | $CH_3$ | Ala |
| | | | $^5CH_2$—$^6CH$ | Sta |
| | | | $^2CH_2$—$^3CH$ | iVa |
| 1.95–2.37 | m | 4 H | $^2CH_2$ | Sta |
| 2.56–3.00 | m | 2 H | $^2CH_2$ | Phe |
| 3.40–3.88 | m | (*) | $CH_3$ | $COOCH_3$ |
| | | | $CH_2$ | Gly |
| | | | $^4CH$—$^3CH$ | Sta |
| 4.08–4.24 | m | 1 H | $^2CH$ | Ala |
| 4.32–4.50 | m | 1 H | $^2CH$ | Phe |
| 4.79 | d | 1 H | OH | Sta |
| 4.90 | d | 1 H | OH | |
| 7.00–7.20 | m | 5 H | aromatic protons | |
| 7.20–7.38 | m | 2 H | 2 NH | |
| 7.83 | d | 1 H | NH | |
| 8.04 | d | 1 H | NH | |
| 8.20 | m | 1 H | NH | |

(*): Integration deficit due to irradiation of the water peak.

The products according to the invention were studied as regards their therapeutic properties and especially their enzyme-inhibiting action. More particularly, the compounds were assessed "in vitro", on the one hand in respect of the inhibition of the human plasma renin activity and on the other hand in respect of the inhibition of porcine pepsin.

A few products were also tested in respect of the inhibition of the cathepsin D activity.

I. METHODS

1. Inhibition of the Human Plasma Renin Activity (P.R.A.)

Our method is inspired by GUYENE (J. Clin. Endocri. Metab. 43, page 1301, 1976) inasmuch as the inhibition of the P.R.A. is evaluated from a pool of human plasma rich in renin (15 to 20 ng of angiotensin I released per milliliter and per hour), incubated at 37° C. in the presence of increasing concentrations of the product to be studied.

The angiotensin I released during the reaction (the human plasma contain and the substrate: angiotensinogen, and the enzyme: renin) is measured by radioimmunological determination using a kit.

Of course, an inhibitor of the enzyme for conversion of the PMSF (phenylmethylsulphonyl fluoride) is added to the incubation medium.

Two types of experiments were carried out:
one at pH 6, which is the optimum pH for the enzyme reaction with human renin (maleate buffer, incubation: 30 minutes), and the other at pH 7.4, which is the physiological pH (phosphate buffer, incubation: 60 minutes).

The results are expressed as the dose of compound, evaluated in mol, which causes a 50% inhibition ($IC_{50}$) of the human plasma renin activity present in the absence of inhibitor.

2. Inhibition of Porcine Pepsin

The method used is that of TAKAAKI AOYAGI (J. Antibiotics, 24, pages 687–694, 1971). The substrate used is bovine haemoglobin and the enzyme is porcine pepsin.

0.5% strength haemoglobin is hydrolysed with pepsin (1 mcg/ml) at 37° C. in 0.02M KCl-HCl buffer at pH 2.

Preincubation takes place for 3 minutes, followed by incubation for 25 minutes. After precipitation of the proteins with 1.7M perchloric acid, the optical density of the supernatant is determined on a spectrophotometer at 280 nm.

The results are expressed as the percentage inhibition of the maximum optical density obtained in the absence of inhibitor. They are also expressed as an $IC_{50}$.

3. Enzyme Inhibition of Cathepsin D

The method used is very similar to the pepsin method (T. AOYAGI, 1971).

The substrate used is bovine haemoglobin and the enzyme is cathepsin D of bovine origin (SIGMA, No.C 3138, batch 26 C-8100).

0.5% strength haemoglobin is hydrolysed with cathepsin D (200 μg/ml) at 37° C. in citrate-phosphate buffer at pH 3.2.

The substrate, the inhibitor and the enzyme are incubated for 30 minutes.

After precipitation of the proteins with 1.7M perchloric acid, the optical density of the supernatant is determined on a spectrophotometer at 280 nm.

The results are expressed as the percentage reduction in the maximum optical density obtained in the absence of inhibitor. The table of results collates the concentrations which cause a 50% inhibition of the maximum effect ($IC_{50}$).

4. Solvents for the Peptides Used for the Three Methods

A $10^{-3}$M stock solution of the peptide is made up in a mixture containing equal volumes of a solution A (19 ml of methanol + 1 ml of acetic acid) and a solution B (4 ml of methanol + 2 ml of sodium hydroxide solution).

The subsequent dilutions of the peptide are then prepared in the appropriate buffer in accordance with the procedures described above.

The amount of solvent present in a solution of the peptide at a concentration below $10^{-4}$M does not interfere with the results.

II. RESULTS

The results obtained with various products of the invention are shown in the following tables, which include the $IC_{50}$ values of each molecule as regards their inhibition of the human plasma renin activity, their inhibition of pepsin and their inhibition of cathepsin D. From 5 to 10 doses were necessary in order to determine these IC50 values. Pepstatine, as a reference substance, is always tested in parallel in each experiment.

TABLE 1

| CODE No. | INHIBITION OF HUMAN P.R.A.* ($IC_{50}$)** | | INHIBITION OF PORCINE PEPSIN ($IC_{50}$) |
|---|---|---|---|
| | pH 6 | pH 7.4 | pH 2 |
| PEPSTATINE | 1.2 to 1.6 × $10^{-6}$ M | 1.2 to 1.4 × $10^{-5}$ M | 1.5 to 2.8 × $10^{-8}$ M |
| SR 41225 | 7 × $10^{-8}$ M | $10^{-6}$ M | 9 × $10^{-8}$ M |
| SR 41320 | 1.7 × $10^{-8}$ M | 3.5 × $10^{-6}$ M | 3 × $10^{-8}$ M |
| SR 41331 | 3.5 × $10^{-9}$ M | 1.9 × $10^{-7}$ M | 1.4 × $10^{-8}$ M |
| SR 41376 | 1.7 × $10^{-8}$ M | 1.5 × $10^{-7}$ M | 1.2 × $10^{-7}$ M |
| SR 41377 | 3 × $10^{-7}$ M | $10^{-5}$ M | 4.7 × $10^{-8}$ M |
| SR 41395 | 1.8 × $10^{-9}$ M | 2.7 × $10^{-8}$ M | 1.3 × $10^{-6}$ M |
| SR 41405 | $10^{-8}$ M | 1.8 × $10^{-7}$ M | 6.5 × $10^{-8}$ M |
| SR 41416 | 8 × $10^{-8}$ M | 1.4 × $10^{-6}$ M | 6.5 × $10^{-8}$ M |
| SR 41476 | 1.7 × $10^{-7}$ M | 2.2 × $10^{-6}$ M | 2.4 × $10^{-8}$ M |
| SR 41477 | 3.5 × $10^{-8}$ M | $10^{-6}$ M | 3.8 × $10^{-8}$ M |
| SR 41485 | 6.75 × $10^{-9}$ M | 1.5 × $10^{-7}$ M | 2.9 × $10^{-8}$ M |
| SR 41491 | 2.6 × $10^{-7}$ M | 4 × $10^{-6}$ M | 2.2 × $10^{-8}$ M |
| SR 41492 | 4 × $10^{-9}$ M | 4.5 × $10^{-8}$ M | 5.5 × $10^{-7}$ M |
| SR 41518 | 9.5 × $10^{-7}$ M | — | 4.8 × $10^{-7}$ M |
| SR 41748 | 2.2 × $10^{-9}$ | 1.1 × $10^{-7}$ | 6.2 × $10^{-7}$ |
| SR 41764 | 1.2 × $10^{-8}$ | 3.1 × $10^{-7}$ | 4.2 × $10^{-8}$ |
| SR 41765 | 3.3 × $10^{-10}$ | 7.5 × $10^{-8}$ | 8.0 × $10^{-9}$ |
| SR 41766 | 1.4 × $10^{-8}$ | 4.2 × $10^{-7}$ | 5.8 × $10^{-8}$ |
| SR 41768 | 5.0 × $10^{-8}$ | 1.0 × $10^{-6}$ | 4.2 × $10^{-8}$ |
| SR 41919 | 2.0 × $10^{-11}$ | 1.1 × $10^{-7}$ | 2.0 × $10^{-8}$ |
| SR 41938 | 1.6 × $10^{-9}$ | 4.4 × $10^{-7}$ | 6.3 × $10^{-8}$ |
| SR 41939 | 1.7 × $10^{-8}$ | 8.8 × $10^{-7}$ | 3.6 × $10^{-8}$ |
| SR 41994 | 7.6 × $10^{-10}$ | 2.6 × $10^{-7}$ | 1.3 × $10^{-8}$ |
| SR 41995 | 3.0 × $10^{-11}$ | 4.2 × $10^{-8}$ | 1.6 × $10^{-8}$ |
| SR 41996 | 1.1 × $10^{-12}$ | 5.1 × $10^{-8}$ | 1.4 × $10^{31\,8}$ |
| SR 42019 | 1.1 × $10^{-7}$ | 3.5 × $10^{-7}$ | 7.3 × $10^{-8}$ |
| SR 42062 | 6.1 × $10^{-8}$ | 1.7 × $10^{-6}$ | 2.6 × $10^{-8}$ |
| SR 42128 | 2.4 × $10^{-13}$ | 2.8 × $10^{-8}$ | 1.9 × $10^{-8}$ |
| SR 42129 | 4.7 × $10^{-10}$ | 3.0 × $10^{-7}$ | 1.6 × $10^{-8}$ |
| SR 42130 | 5.2 × $10^{-8}$ | 2.6 × $10^{-6}$ | 2.7 × $10^{-8}$ |
| SR 42238 | 2.1 × $10^{-9}$ | 1.9 × $10^{-7}$ | 2.1 × $10^{-8}$ |
| SR 42256 | 2.6 × $10^{-8}$ | 4.8 × $10^{-7}$ | 2.7 × $10^{-8}$ |
| SR 42258 | 9.0 × $10^{-9}$ | 4.7 × $10^{-7}$ | 1.8 × $10^{-8}$ |
| SR 42261 | 1.7 × $10^{-7}$ | 4.7 × $10^{-6}$ | 7.5 × $10^{-7}$ |
| SR 42286 | 1.2 × $10^{-6}$ | 1.1 × $10^{-5}$ | > $10^{-5}$ |

*P.R.A. = plasma renin activity
**$IC_{50}$ = dose which causes 50% inhibition of the effect serving as the reference.

TABLE 2

INHIBITION OF THE ENZYME ACTIVITY OF CATHEPSIN D

| CODE No. | FORMULA | $IC_{50}$ |
|---|---|---|
| SR 41331 | Boc—Phe—Phe—Sta—Ala—Sta—OMe | 1.8 × $10^{-7}$ M |
| SR 41376 | Boc—Trp—Trp—Sta—Ala—Sta—OMe | 1.3 × $10^{-7}$ M |
| SR 41395 | Boc—Phe—His—Sta—Ala—Sta—OMe | 8.7 × $10^{-7}$ M |
| SR 41405 | Z—Phe—Val—Sta—Ala—Sta—OMe | 9.5 × $10^{-8}$ M |
| SR 41485 | Z—Trp—Val—Sta—Ala—Sta—OMe | 7.5 × $10^{-8}$ M |
| SR 41492 | Boc—Phe—His—Sta—Ala—Sta—OH | 7.0 × $10^{-7}$ M |
| SR 41619 | Boc—Trp—His—Sta—Ala—Sta—OMe | 7.5 × $10^{-7}$ M |
| PEPSTATINE | Iv—Val—Val—Sta—Ala—Sta | 6.2 × $10^{-8}$ M |

The compounds of the present invention have a very substantial inhibiting action on the human plasma renin activity and this action is generally distinctly greater than that of the natural product pepstatine: in this respect, they can be used in the treatment of arterial hypertension.

They also possess a pronounced inhibiting action on acid proteases, in particular pepsin and cathepsin D. It is therefore possible to envisage the use of the products according to the invention in fields of therapy where the inhibition of such enzyme systems is justified, in particular (in addition to arterial hypertension) gastroduodenal ulcers and inflammatory complaints.

The peptides of the present invention can be used in therapy by intravenous, intramuscular or subcutaneous injection. They are used in a solvent such as physiological serum (isotonic saline solution) or in a buffer such as phosphate buffer.

The amount of active principle to be used varies according to the desired therapeutic effects, the seriousness of the complaint to be treated and the chosen method of administration. It must be determined for each patient and is most frequently between 1 and 100 mg of active principle.

We claim:

1. Peptide derivatives of the general formula:

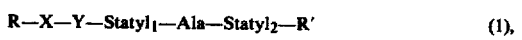

in which:

Statyl$_1$ represents the radical derived from the aminoacid statine, of the formula

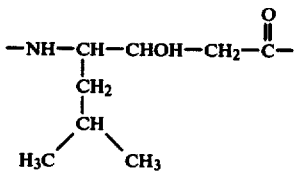

3S,4S isomer and Statyl$_2$ denotes the statyl radical derived from the same aminoacid, but can be the 3S,4S isomer or the 3R,4S isomer, R denotes a hydrogen atom or an acylating group attached to the terminal amino group of the aminoacid X—, X and Y, which are identical or different, denote aminoacids chosen from the following aminoacids:

X: Phenylalanine, Tryptophan, Histidine, Boc-Histidine, Tyrosine, Proline, Isoleucine, and Y: Phenylalanine, Tryptophan, Histidine, Tyrosine, Proline, Leucine, Isoleucine, Norleucine, Valine, Norvaline, Alanine, Glycine, Lysine, Z-lysine and α-Aminobutyric acid, and R' represents OH, O-lower alkyl, NH$_2$ or a group NH—R$_1$, in which R$_1$ represent a lower alkyl or lower aralkyl group, and the pharmaceutically acceptable salts of the products of the formula (1) when R' represents OH.

2. Peptide derivatives according to claim 1, in which R represents a group chosen from amongst the following groups: acetyl (Ac), isovaleryl (iva), octyl, t-butylacetyl, t-butoxycarbonyl (Boc), adamantyloxycarbonyl (Adoc), benzyloxycarbonyl (Z), benzyloxycarbonyl)-β-aminoethylsulphonyl (Z-Tau), (t-butoxycarbonyl)-β-aminoethylsulphonyl (Boc-Tau), phenylsulphonyl, benzylsulphonyl and 3-phenylpropionyl.

3. A composition of matter for treatment of arterial pressure and digestive diseases comprising a peptide derivative as defined in claim 1 and a pharmaceutically acceptable carrier.

4. The composition of claim 3, wherein said peptide derivative is present in an amount from 1 to 100 mg.

5. A method for the treatment of arterial pressure comprising administering to a patient an effective amount of a peptide derivative as defined in claim 1.

6. A method of treating digestive diseases comprising administering to a patient an effective amount of a peptide derivative as defined in claim 1.

* * * * *